United States Patent [19]

Yu et al.

[11] Patent Number: 5,508,311
[45] Date of Patent: *Apr. 16, 1996

[54] ALIPHATIC PROPARGYLAMINES AS SELECTIVE MAO-B INHIBITORS AND AS NEUROPROTECTIVE AGENTS

[75] Inventors: Peter H. Yu; Bruce A. Davis; Alan A. Boulton, all of Saskatoon, Canada

[73] Assignee: University of Saskatchewan, Saskatoon, Canada

[ * ] Notice: The term of this patent shall not extend beyond the expiration date of Pat. No. 5,169,868.

[21] Appl. No.: 108,653

[22] PCT Filed: Feb. 28, 1992

[86] PCT No.: PCT/CA92/00090

§ 371 Date: Dec. 23, 1993

§ 102(e) Date: Dec. 23, 1993

[87] PCT Pub. No.: WO92/15551

PCT Pub. Date: Sep. 17, 1992

Related U.S. Application Data

[63] Continuation of Ser. No. 663,018, Mar. 1, 1991, Pat. No. 5,169,868.

[51] Int. Cl.⁶ ..................................... A61K 31/13
[52] U.S. Cl. ......................... 514/671; 514/672; 564/509; 564/510
[58] Field of Search .................................. 514/671, 672; 564/509, 510

[56] References Cited

U.S. PATENT DOCUMENTS

| | | | |
|---|---|---|---|
| 4,201,725 | 5/1980 | Pigerol et al. | 260/583 H |
| 4,650,907 | 3/1987 | Bey et al. | 564/509 |
| 5,196,583 | 3/1993 | Yamada et al. | 564/305 |

FOREIGN PATENT DOCUMENTS

| | | |
|---|---|---|
| 431700A2 | 6/1991 | European Pat. Off. . |
| 1453844 | 3/1965 | France . |
| M-444 | 6/1965 | France . |
| 842651 | 4/1957 | United Kingdom . |

OTHER PUBLICATIONS

Yu Peter, "Deamination of aliphatic amines of different chain lengths by rat liver monoamine oxidase A and B", J. Pharm. Pharmacol 1989, vol. 41, pp. 205–208.

Youdim et al, "New directions in monoamine oxidase A and B . . .", Biochemical Pharmacology, vol. 41, No. 2, 1991, pp. 155–162.

Youdim et al, "The role of monoamine oxidase, iron–melanin interaction . . .", J. Neural Transm (1990) (Suppl), vol. 32, 1990, pp. 239–248.

Boissier et al, "Synthesis of new monoamine oxidase inhibitors", Checmical Abstracts, vol. 67, No. 13, Abstracts No. 63889a, 1966.

Chemical Abstracts, Ninth Collective Index, vol. 76–85, 1972–1976, p. 14321CS.

Shita et al, "Metabolism of the neurotoxic tertiary amine, MPTP, by . . .", Biochemical and Biophysical Research Communications, vol. 120, No. 2, 1984.

Primary Examiner—Richard L. Raymond
Attorney, Agent, or Firm—Larson and Taylor

[57] ABSTRACT

The invention relates to a series of propargylamines, their salts and pharmaceutical compositions containing a compound of formula (III) wherein $R_1$, $R_3$ and $R_4$ are the same or different and represent hydrogen or a straight chain or branched lower alkyl; y is an integer ranging from 0 to 5; z is an integer ranging from 0 to 5; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which form 1 to 3 are heteroatoms selected from O, S and/or N, and pharmaceutically acceptable salts thereof, in admixture with a pharmaceutically acceptable carrier, excipient or adjuvant. The compounds are useful as selective monoamine oxidase B inhibitors and have demonstrated neuroprotective properties in human and veterinary medicine.

30 Claims, No Drawings

ALIPHATIC PROPARGYLAMINES AS SELECTIVE MAO-B INHIBITORS AND AS NEUROPROTECTIVE AGENTS

This is a continuation of Ser. No. 663,018 filed Mar. 30, 1991, now Pat. No. 5,169,868.

FIELD OF THE INVENTION

The invention relates to a series of aliphatic propargylamines, their salts and to pharmaceutical compositions containing such compounds. The compounds are useful as selective monoamine oxidase B inhibitors and have demonstrated neuroprotective properties in human and veterinary medicine.

BACKGROUND OF THE INVENTION

Monoamine oxidase (MAO) is an enzyme that oxidizes monoamine neurotransmitters and neuromodulators, as well as exogenous bioactive monoamines. It was first characterized by Hare in 1928 and was later called MAO by Zeller in 1938. Following the characterization of this enzyme, it was later discovered that its inhibition could have positive effects on psychiatric disorders such as depression.

Iproniazid, described in the late 1950's and used as a treatment for tuberculosis, was found to have mood-elevating properties. It was later shown to be a suitable MAO inhibitor and was used thereafter as an effective antidepressant. However, the drug had to be withdrawn from the U.S. market in the early 1960's because of the reports of hepatic toxicity and occasional hypertensive crises associated with its use. Still, the success of Iproniazid as an antidepressant stimulated pharmaceutical companies to search for new MAO inhibitors having antidepressant properties without adverse side effects. Since then, a large number of MAO inhibitors have been synthesized and administered.

Until 1972, when it was discovered for the first time that MAO existed in two forms, namely MAO-A and MAO-B, the first generation of MAO inhibitors had no selective inhibitory activity towards MAO-A and/or MAO-B. Examples of these compounds are the drugs phenelzine and tranylcypromine, respectively patented in 1959 (U.S. Pat. No. 3,000,903) and 1961 (U.S. Pat. No. 2,997,422). Apart from inhibiting the activity of both MAO-A and MAO-B, these non-selective irreversible MAO inhibitor antidepressants also exhibit other important drawbacks. Hence, these drugs have been categorized as "dirty" drugs. In other words, they also block other enzymes and most importantly, they can, similarly to Iproniazid, cause severe hepatotoxicity and hypertension resulting from the ingestion of tyraminerich food and drinks. This is caused by the fact that dietary amines are not broken down after ingestion and thus release circulating catecholamines which may lead to hypertensive crises and sometimes death. Thus, non-selective MAO inhibitors of this type have acquired a bad reputation and although they are very effective antidepressants, they have been avoided by most psychiatrists in favour of the relatively safer tricyclic antidepressants.

In the mid 1960's, a French group headed by Jacques R. Boissier published data on the synthesis of three series of new aliphatic and cycloaliphatic derivatives of hydrazine, propargylamine and cyclopropylamine, suspected to be useful as monoamine oxidase inhibitors (Chimie Therapeutique (1966), 320–326). Boissier et al. suggested that these non-selective total MAO inhibitors might possess therapeutic properties for the treatment of depression or angina pain. In French Patent 1,453,844, N-propynylalkylamines having a linear or branched alkyl group of 6 to 9 carbon atoms on the amino moiety are described.

In a further 1967 publication (Therapie, XXII, 1967, 367–373), Boissier et al. reported the results of tests conducted with these compounds to evaluate their antidepressant activity. Based on the results obtained, Boissier et al. concluded that the aliphatic compounds of the propargylamine series were practically inactive in vivo, regardless of whether the amine was secondary or tertiary, and only moderately active in vitro. From these results, it seemed that a promising future could not be foreseen for aliphatic propargylamines as effective MAO inhibitors. Hence, research involving compounds of this type was completely abandoned after the 1965, '66 and '67 publications by Boissier et al. It turned out that most of the research done later on MAO inhibitors concentrated on aromatic compounds.

In the early 1970's, it gradually became apparent that MAO existed in multiple forms, namely MAO-A and MAO-B. These two types of enzymes have been found to be somewhat different from one another. They exhibit different substrate profiles, they respond differently to selective inhibitors, they are found in different cellular and subcellular locations and they are distributed differently between neuronal and non-neuronal structures. Recently, MAO-A and MAO-B have been shown to arise from different gene loci. MAO-A is located predominantly inside the neurones and is responsible for causing hypertensive crises. It preferentially deaminates and oxidizes 5-hydroxytryptamine. As for MAO-B, it is found mostly in glia and it preferentially oxidizes $\beta$-phenylethylamine.

The discovery of MAO-A and MAO-B was of major importance since it initiated the research that led to the synthesis of second generation MAO inhibitors. The second generation MAO inhibitors are compounds that irreversibly or reversibly inhibit either the A or the B form of the enzyme. Because both the antidepressant and hypertensive effects are considered to be related to the inhibition of MAO-A, drug companies have concentrated their efforts mainly in the development of MAO-A inhibitors. Clorgyline, Lilly 51641 and PCO were among the first selective MAO inhibitors for MAO-A to be discovered. All these compounds belong to the first category of second generation MAO inhibitors and form irreversible links with the A enzyme.

The reversible specific MAO inhibitors, which form the second category of second generation inhibitors, have recently attracted attention because of their potentially improved clinical properties. Included in this category are harmine, harmaline, cimoxatone, brofaromine, amiflamine and moclobemide.

In recent years, a MAO-A inhibitory prodrug has also been discovered. MDL-72394 can be decarboxylated by aromatic L-amino acid decarboxylase and forms a potent irreversible MAO-A inhibitor, which has been shown to be neuronal selective. The chemical structures of first and second generation aromatic MAO-A and -B inhibitors may be found in Chapter 7 of Neuromethods, Volume 5, Neurotransmitter Enzymes, 1986, Humana Press, the contents of which is hereby incorporated by reference.

Research on MAO-B inhibitors is nowhere near the level of research accomplished so far for MAO-A. In fact, only a few irreversible MAO-B inhibitors such as Deprenyl and Pargyline have so far been discovered. Deprenyl is one of the most important and widely tested MAO-B inhibitors. It has been used as an effective adjuvant to L-DOPA in the treatment of Parkinson's disease. The combination of Deprenyl and L-DOPA seems to reduce the requirement for L-DOPA (presently known to be the best antiparkinsonian agent) in those cases where L-DOPA is being ingested. Recently, it was reported that Deprenyl alone can significantly delay the onset of disability associated with early, otherwise, untreated cases of Parkinson's disease. It has also been claimed that the use of Deprenyl improved the clinical condition of some Alzheimer's patients and reduced depression, attention deficit disorders and potentially other neuropsychiatric disorders. In addition, Deprenyl has been observed to prolong life span and sexual activity in animals and humans. Unlike MAO-A inhibitors, MAO-B inhibitors do not usually cause hypertensive crises except, in some instances, under chronic large-dose applications and therefore have the potential to become very useful neuropsychiatric and geriatric drugs.

Although Deprenyl at higher doses can cause a slight increase in dopamine levels in the brain, the involvement of dopamine in the mechanism of action of Deprenyl has not been well established. The inhibition of MAO-B activity causes a selective accumulation of β-phenylethylamine, a typical MAO-B substrate, which is present endogenously, including in the central nervous system. β-Phenylethylamine, which possesses stimulant properties, can amplify dopaminergic function and modulate dopaminergic neurotransmission and is therefore related to the chemotherapy of MAO-B inhibitors.

It was also found that since Deprenyl is a structural analog of amphetamine, it is catabolized to produce small amounts of amphetamine. This has caused some concern because it was hypothesized that Deprenyl might, in some instances, be a drug subject to substance abuse. Hence, different MAO-B inhibitors not possessing amphetamine-like properties are required. Recently, the reversible MAO-B inhibitors MD 780236 and RO-16-6491 as well as the irreversible inhibitor MDL-72145 were discovered but other alternatives are still being sought. Recent studies on currently available MAO-A and MAO-B inhibitors are summarized in Youdim et al., (1991) Biochemical Pharmacology, Vol. 41, No. 2, pp. 133–162, which is hereby incorporated by reference.

In 1989, the results of a systematic investigation on the deamination by MAO-A and -B of amines having aliphatic chains of various lengths were published (J. Pharm. Pharmacol. 1989, 41:205–208). It was found that these amines were readily oxidized by MAO-B with very high affinity. The deamination of these aliphatic amines by MAO-B was found to be even more sensitive to Deprenyl than that of β-phenylethylamine, which is known to be a typical MAO-B substrate. Unfortunately, although these compounds were found to be good substrates for MAO-B, they did not exhibit any inhibitory activity towards this enzyme.

In summary, active research on MAO inhibitors has been carried out since as early as 1950 and hundreds of potentially useful MAO inhibitors have been synthesized. There was an important change in research focus in the early 1970's when the existence of two different forms of MAO enzymes was discovered. It seems that substantial progress has been made in MAO-A inhibition but much more work remains to be done to find suitable MAO-B inhibitors. Since the inhibition of MAO-B appears to alleviate the symptoms of aging associated diseases such as Parkinson's disease and Alzheimer's disease, suitable MAO-B inhibitors would be highly desirable, especially in view of the limited and relatively inefficient treatments available for these diseases.

The central nervous system, particularly the dopamine system, has received considerable attention in the field of age-related neuronal degeneration and neurodegenerative conditions, such as Parkinson's disease, Alzheimer's disease, etc. Several neurochemical markers of the brain's dopaminergic system, such as dopamine levels, activity of the key enzyme tyrosine hydrolase, densities of dopamine receptors and the dopamine uptake system are all found to be reduced in the normal aging process (Morgan and Finch, Ann. N.Y. Acad. Sci. 515 (1988):145–60) and in neurodegenerative disorders. Changes to these markers are the result of neuronal death in specific regions of the brain. These neuronal losses are irreversible and the intensity of the damage increases with age. The cause of the cell death is unknown. When dopamine neurone numbers are reduced to about 20% of controls in the striatum, for example, pathological movement disorders begin to appear (i.e. Parkinson's disease). Although the symptoms of this disease can be treated with 1-dopa, it unfortunately is only beneficial for a limited period of about three to five years. Cell death and neuronal degeneration continues in a progressive manner and several hypotheses regarding this have been proposed. MPTP was found to cause Parkinson's disease (Langston, Science 225 (1984):1480–1482) and it has been suggested that the disease could perhaps be caused by MPTP-like substances to which patients have been exposed or that perhaps these substances could be generated endogenously (Snyder and D'Amato, Neurol. 36 (1984):250–258). MPTP is converted by MAO-B in the brain to $MPP^+$, which is considered to be a distal toxin. Blocking MAO-B activity, therefore, prevents neurons from damage by MPTP-like neurotoxins. In one animal study deprenyl has been shown to protect dopamine neurons even after the MPTP has been completely washed out of the tissues (Tatton, 3rd Can. Conf. Neurodegenerative Diseases, PD, (abstract) Toronto). The mechanism of this neuroprotective effect has yet to be determined.

Neuronal degeneration may be caused by an increase in oxidative stress derived from MAO-catalyzed oxidative deamination of dopamine and other amines. In these reactions, hydrogen peroxide is produced as a side product. In the presence of metal ions, such as ferrous, hydrogen peroxide is converted to hydroxyl free radical, an extremely reactive substance, which causes lipid peroxidation and subsequent harmful oxidative chain reactions. Such reactions cause damage to the cellular components of cells, particularly mitochondrial membranes, and thus they destroy neurons. The produced toxic and harmful oxygen peroxide can be detoxified in various ways, such as removal via reaction with reduced glutathione (GSH) to produce oxidized glutathione (GSSH) or by catalase ($H_2O_2 \rightarrow H_2O + O_2$) or by peroxidase ($R(OH)_2 + H_2O_2 \rightarrow H_2O + RO_2$). It is of interest to note that both $H_2O_2$ and oxidized glutathione are found to increase with ageing (Sohal and Allen, In The molecular basis of ageing, pp 75–104, eds Woodheat et al, Plenum Press, N.Y. 1985). Iron has been shown to be elevated in the postmortem brain of PD patients (Dexter et al, J. Neurochem. 52 (1989):1830–1836). One cannot simply administer Fe chelators, however, as a way to reduce neurodegeneration because of the possibility of serious unwanted side effects. Iron is an essential cofactor in many vital enzymes. MAO-B activity is known to be elevated in ageing brain (Fowler et al, J. Neural Transm. 49 (1980):1–20) and this suggests that the ageing brain suffers oxidative stress due to excessive deamination. Reduction of such stress (i.e. caused by $H_2O_2$) by inhibiting MAO-catalyzed deamination reactions, might seem therefore rational as a treatment to reduce oxidative stress and neuronal deterioration.

SUMMARY OF THE INVENTION

The present invention relates to a compound having the following formula I:

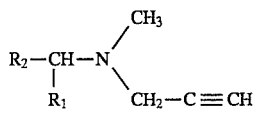

wherein $R_1$ is hydrogen or a straight chain or branched lower alkyl; and $R_2$ is a straight chain or branched alkyl, alkenyl, alkynyl, alkoxy, alkylthio or alkyl sulphinyl group having from 3 to 11 carbon atoms. $R_2$ is unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, with the provisos that:

when $R_1$ is $CH_3$, $R_2$ is not an unsubstituted alkyl having from 4 to 7 carbon atoms, and when $R_2$ is substituted with carboxyl or loweracyloxy, the carboxyl or loweracyloxy substituent is not on the last atom of the longest chain of the $R_2$ group.

$R_1$ is preferably a lower alkyl having between 1 and 4 carbon atoms. $R_2$ is preferably a straight chain or branched alkyl, alkenyl, alkynyl or alkoxy, unsubstituted or substituted with at least one halogen selected from fluorine, chlorine, bromine and iodine.

Preferred compounds include those falling within the scope of the following formula II:

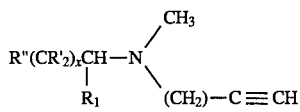

wherein x is an integer ranging from 1 to 2 or 7 to 13;

$R_1$ represents hydrogen or a straight chain or branched lower alkyl having from 1 to 4 carbon atoms and preferably methyl;

R' represents H or halogen; and

R" represents methyl, hydrogen or halogen, and pharmaceutically acceptable salts thereof.

Most preferred compounds are:
N-(1-butyl)-N-methylpropargylamine-HCl (1-BuMP)
N-(2-butyl)-N-methylpropargylamine-HCl (2-BuMP)
N-(2-pentyl)-N-methylpropargylamine-HCl (M-2-PP)
N-(1-pentyl)-N-methylpropargylamine-oxalate (M-1-PP)
N-(2-decyl)-N-methylpropargylamine-HCl (2-DMP)
N-(2-dodecyl)-N-methylpropargylamine-HCl (2-DdMP) and
R (−)-N-(2-butyl)-N-methylpropargylamine-oxalate (R-(−)2-BuMP).

The compounds of the present invention have been found to be highly potent, irreversible, selective MAO-B inhibitors. These novel MAO-B inhibitors are characterized by having a chemical structure that is not amphetamine-like. They can therefore block MAO-B activity but without any amphetaminergic effect.

The compounds of the present invention have also been found to be useful for the treatment and prevention of neurodegenerative disorders by acting as neuroprotective agents. Preferably, the compounds are useful in preventing mammalian neuron cell degeneration resulting from the action of neurotoxic substances either found in the environment mostly as toxic pollutants or generated endogenously.

The compounds of the present invention may therefore be used in the treatment of various neuropsychiatric disorders in humans or animals, such as Parkinsonism, Alzheimer's disease, depression, attention deficit disorders, hyperactive disorders, aging and to improve the quality of life in humans or animals.

Particularly, aliphatic propargylamines with short (x=1 to 2) or long (x=7 to 13) carbon chains have been found to be unexpectedly efficient in inhibiting MAO-B activity. The potency of MAO inhibitory activity in vitro increases with the increase of carbon chain length of the aliphatic group on the left hand side of the molecule. However, it seems that the compounds with short aliphatic chains are less easily absorbed and more readily transported into the brain in vivo and could therefore be more effective in blocking MAO-B activity following oral administration.

Thus, although aliphatic propargylamines with short carbon chains are less effective MAO-B inhibitors in vitro, they become significantly more active when they are administered peripherally and especially after oral ingestion. Such in vitro and in vivo data indicate that the pharmacokinetic properties of the short chain aliphatic MAO-B inhibitors are distinctly different from those of the longer aliphatic propargylamines and Deprenyl. This aspect is particularly desirable in clinical applications.

With regard to the long carbon chain propargylamines, although they appear to be less potent at inhibiting MAO-B activity after acute administration, and this perhaps may be due to increased absorption, they are slowly released thereafter and may thus be useful from a chronic treatment point of view.

Another worthwhile aspect to note is that the selectivity of some of these compounds towards MAO-B is significantly higher than for Deprenyl. This is very important since it reduces or eliminates any possible hypertensive effects even after chronic treatment.

As it will be explained in further detail later on, some positional isomers and enantiomers of the compounds of the present invention have been found to be considerably more active than other positional isomers and enantiomers. For example, it seems that in the aliphatic propargylamines harboring short aliphatic chains, the 1-alkyl propargylamines are substantially more selective than the 2-alkyl propargylamines whereas in the case of the aliphatic propargylamines bearing long aliphatic chains, the 2-alkyl compound seems to be more potent and more selective than the 1-alkyl compounds. Furthermore, data obtained so far tends to show that the R(−)-enantiomer is substantially more active than the S(+)-form in the inhibition of MAO-B activity. Therefore, preferred compounds of the present invention are the R(−)-enantiomers of the compounds of formula II.

The present invention also relates to a pharmaceutical composition for the in vivo inhibition of MAO-B activity in mammals. The composition comprises an effective amount of a compound having the following formula I:

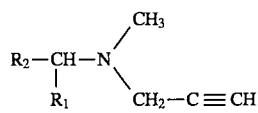

wherein $R_1$ is hydrogen or a straight chain or branched lower alkyl; and $R_2$ is a straight chain or branched alkyl, alkenyl, alkynyl, alkoxy, alkylthio or alkyl sulphinyl group having from 3 to 11 carbon atoms. $R_2$ is unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, in admixture with a pharmaceutically acceptable carrier, excipient or adjuvant, with the provisos that:

when $R_1$ is $CH_3$, $R_2$ cannot be an unsubstituted alkyl having from 4 to 7 carbon atoms, and when $R_2$ is substituted with carboxyl or loweracyloxy, the carboxyl or loweracyloxy substituent is not on the last atom of the longest chain of the $R_2$ group.

$R_1$ is preferably a lower alkyl having between 1 and 4 carbon atoms. $R_2$ is preferably a straight chain or branched alkyl, alkenyl, alkynyl or alkoxy, unsubstituted or substituted with at least one halogen selected from fluorine, chlorine, bromine and iodine.

Preferred compounds used in the composition of the present invention include those falling within the scope of the following formula II:

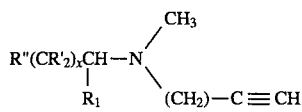

wherein x is an integer ranging from 1 to 2 or 7 to 13;

$R_1$ represents hydrogen or a straight chain or branched lower alkyl having from 1 to 4 carbon atoms, preferably methyl;

R' represents H or halogen; and

R" represents methyl, hydrogen or halogen, and pharmaceutically acceptable salts thereof, in admixture with a pharmaceutically acceptable carrier, excipient or adjuvant.

Most preferred compounds comprised within the above-mentioned pharmaceutical composition include:

N-(1-butyl)-N-methylpropargylamine-HCl (1-BuMP)
N-(2-butyl)-N-methylpropargylamine-HCl (2-BuMP)
N-(2-pentyl)-N-methylpropargylamine-HCl (M-2-PP)
N-(1-pentyl)-N-methylpropargylamine-oxalate (M-1-PP)
N-(2-decyl)-N-methylpropargylamine-HCl (2-DMP)
N-(2-dodecyl)-N-methylpropargylamine-HCl (2-DdMP) and
R-(–)-N-(2-butyl)-N-methylpropargylamine-oxalate (R-(–)-2-BuMP).

The compositions described above have been found to be useful to selectively and irreversibly inhibit MAO-B. These findings are unexpected, especially in view of the comments of Boissier et al. in Therapie XXII, 1967, 367–373. Boissier et al. had found aliphatic propargylamines to be practically inactive in vivo regardless of whether the amine is secondary or tertiary and only moderately active in vitro. As mentioned previously, it has been found that the compounds with short aliphatic chains and long aliphatic chains exhibit different pharmacological properties.

The pharmaceutical compositions of the present invention are also useful in the treatment and prevention of neurodegenerative disorders by acting as neuroprotective agents.

The present invention also relates to a method for the in vivo inhibition of MAO-B to alleviate neuropsychiatric disorders such as Parkinsonism in mammalian subjects, preferably in human subjects. The method comprises administering to a mammalian subject an effective amount of the compound having the following formula I:

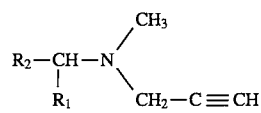

wherein $R_1$ is hydrogen or a straight chain or branched lower alkyl; and $R_2$ is a straight chain or branched alkyl, alkenyl, alkynyl, alkoxy, alkylthio or alkyl sulphinyl group having from 3 to 11 carbon atoms. $R_2$ is unsubstituted or substituted with at least one of the substituents selected from hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, with the proviso that:

when $R_2$ is substituted with carboxyl or loweracyloxy, the carboxyl or loweracyloxy substituent is not on the last atom of the longest chain of the $R_2$ group.

$R_1$ is preferably a lower alkyl having between 1 and 4 carbon atoms. $R_2$ is preferably a straight chain or branched alkyl, alkenyl, alkynyl or alkoxy, unsubstituted or substituted with at least one halogen selected from fluorine, chlorine, bromine and iodine.

Preferred compounds used in this method include those falling within the scope of the following formula II:

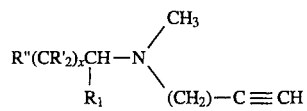

wherein x is an integer ranging from 1 to 13;

$R_1$ represents hydrogen or a straight chain or branched lower alkyl having from 1 to 4 carbon atoms, preferably methyl;

R' represents H or halogen and

R" represents methyl, hydrogen or halogen, and pharmaceutically acceptable salts thereof.

Most preferred compounds within the scope of this method include:

N-(1-butyl)-N-methylpropargylamine-HCl (1-BuMP)
N-(2-butyl)-N-methylpropargylamine-HCl (2-BuMP)

N-(2-pentyl)-N-methylpropargylamine-HCl (M-2-PP)
N-(1-pentyl)-N-methylpropargylamine-oxalate (M-1-PP)
N-(2-hexyl)-N-methylpropargylamine-HCl (2-HxMP)
N-(2-heptyl)-N-methylpropargylamine-HCl (2-HMP)
N-(2-decyl)-N-methylpropargylamine-HCl (2-DMP)
N-(2-dodecyl)-N-methylpropargylamine-HCl (2-DdMP) and
R(-)-N-(2-butyl)-N-methylpropargylamine-oxalate (R-(-)-2-BuMP).

Also within the scope of the present invention is the use of a compound of formulae I or II in the in vivo inhibition of MAO-B to alleviate neuropsychiatric disorders in mammalian subjects and the use of a compound of formulae I or II for the preparation of a medicament useful for in vivo inhibition of MAO-B to alleviate neuropsychiatric disorders in mammalian subjects.

The present invention also relates to a method for preventing the premature degeneration of neuron cells in mammalian subjects, preferably in human subjects. The method comprises administering to a mammalian subject a compound according to the following formula III:

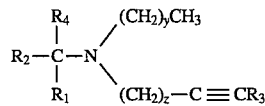

wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms. $R_2$ is unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, in admixture with a pharmaceutically acceptable carrier, excipient or adjuvant.

$R_1$ is preferably a lower alkyl having between 1 and 4 carbon atoms. $R_2$ is preferably a straight chain or branched alkyl, alkenyl, alkynyl or alkoxy, unsubstituted or substituted with at least one halogen selected from fluorine, chlorine, bromine and iodine.

$R_3$ and $R_4$ are preferably hydrogen and y is preferably 0 and z is preferably 1.

Preferred compounds used in this method include those falling within the scope of the following formula IV:

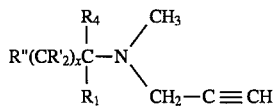

wherein x is an integer ranging from 1 to 13;

$R_1$ and $R_4$ are the same or different and represent hydrogen or a straight chain or branched lower alkyl; and R' represents H or halogen, R" represents methyl, hydrogen or halogen, and pharmaceutically acceptable salts thereof.

Most preferred compounds falling within the scope of this method include:

N-(2-pentyl)-N-methylpropargylamine-HCl (M-2-PP)
N-(1-pentyl)-N-methylpropargylamine-oxalate (M-1-PP) and
N-(2-hexyl)-N-methylpropargylamine-HCl (2-HxMP).

Also within the scope of the present invention is the use of the compounds of formulae III and IV in preventing the premature degeneration of neuron cells in mammalian subjects and the use of a compound of formulae III and IV for the preparation of a medicament used for the prevention of premature neuron cell degeneration in mammals.

The present invention also relates to a method for protecting mammalian neuron cells from the action of neurotoxic agents causing neurodegenerative disorders to mammals subjected to such neurotoxic agents. The method comprises administering to a mammalian subject a compound having the following formula III:

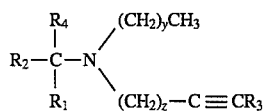

wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms. $R_2$ is unsubstituted or substituted with at least one of the substituents selected from hydroxy, aldehyde, oxo, lower acyloxy, halogen, thio, sulfoxide, sulfone, phenyl, halogensubstituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, in admixture with a pharmaceutically acceptable carrier, excipient or adjuvant.

$R_1$ is preferably a lower alkyl having between 1 and 4 carbon atoms. $R_2$ is preferably a straight chain or branched alkyl, alkenyl, alkynyl or alkoxy, unsubstituted or substituted with at least one halogen selected from fluorine, chlorine, bromine and iodine.

$R_3$ and $R_4$ are preferably hydrogen and y is preferably 0 and z is preferably 1.

Preferred compounds used in this method include those falling within the scope of the following formula IV:

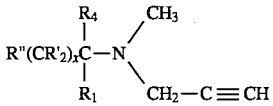

wherein x is an integer ranging from 1 to 13;

$R_1$ and $R_4$ are the same or different and represent hydrogen or a straight chain or branched lower alkyl;

R' represents H or halogen; and

R" represents H, halogen or methyl, and pharmaceutically acceptable salts thereof, in admixture with a pharmaceutically acceptable carrier, excipient or adjuvant.

Most preferred compounds include:
N-(2-pentyl)-N-methylpropargylamine-HCl (M-2-PP)
N-(1-pentyl)-N-methylpropargylamine-oxalate (M-1-PP) and N-(2-hexyl)-N-methylpropargylamine-HCl (2-HxMP).

Also within the scope of the present invention is the use of the compounds of formulae III or IV in protecting mammalian neuron cells from the action of neurotoxic agents causing neurodegenerative disorders to mammals and the use of the compounds of formulae III and IV for the preparation of a medicament used for protecting mammalian neuron cells from the action of neurotoxic agents causing neurodegenerative disorders to mammals.

Neuron cells that can be protected and even rescued using the method of the present invention possibly include aminergic and non-aminergic neurons, preferably those containing dopamine and noradrenaline. The wide spectrum of action of the compounds of the present invention, by being useful to protect and rescue various types of neuron cells, makes the compounds particularly useful for broad spectrum neuroprotective therapies.

The present invention therefore relates to a method for the treatment of neurodegenerative disorders in mammals. The method comprises administering to a patient a compound having the following formula III:

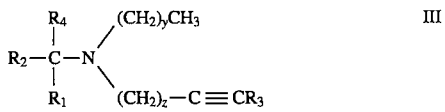

wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms. $R_2$ is unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, in admixture with a pharmaceutically acceptable carrier, excipient or adjuvant.

$R_1$ is preferably a lower alkyl having between 1 and 4 carbon atoms. $R_2$ is preferably a straight chain or branched alkyl, alkenyl, alkynyl or alkoxy, unsubstituted or substituted with at least one halogen selected from fluorine, chlorine, bromine and iodine.

$R_3$ and $R_4$ are preferably hydrogen and y is preferably 0 and z is preferably 1.

Preferred compounds used in this method include those falling within the scope of the following formula IV:

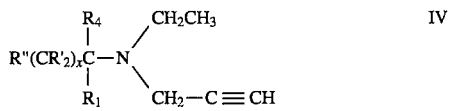

wherein x is an integer ranging from 1 to 13;

$R_1$ and $R_4$ are the same or different and represent hydrogen or a straight chain or branched lower alkyl;

R' represents H or halogen; and

R" represents H, halogen or methyl, and pharmaceutically acceptable salts thereof.

Most preferred compounds include:

N-(2-pentyl)-N-methylpropargylamine-HCl (M-2-PP)

N-(1-pentyl)-N-methylpropargylamine-oxalate (M-1-PP) and

N-(2-hexyl)-N-methylpropargylamine-HCl (2-HxMP).

When used in the context of the present invention, the term "neurodegenerative disease" is intended to include any neurological disorder involving the premature or accelerated degeneration of neuron cells. Such disorders include Alzheimer's disease, Parkinson's disease, Huntington's disease, motor neurone disease as well as ischaemia, stroke and accelerative aging.

Also within the scope of the present invention is the use of the compounds of formula III and IV in the treatment of neurodegenerative disorders in mammals and the use of compounds of formula III and IV for the preparation of a medicament used for the treatment of neurodegenerative disorders in mammals.

The present invention also relates to a commercial package for the in vivo inhibition of MAO-B to alleviate neuropsychiatric disorders in mammals. The package comprises a pharmaceutical agent therapeutically effective in the in vivo inhibition of MAO-B to alleviate neuropsychiatric disorders in mammals together with instructions to use the pharmaceutical agent in the in vivo of inhibition of MAO-B to alleviate neuropsychiatric disorders in mammals. The pharmaceutical agent comprised in the commercial package is a propargylamine derivatives or a pharmaceutically effective salt thereof corresponding to the compound of formulae I or II referred to previously. If required, the pharmaceutical agent is admixed with a pharmaceutically acceptable carrier, excipient or adjuvant.

The present invention also relates to a commercial package for the treatment or prevention of neurodegenerative disorders in mammals. The package comprises a pharmaceutical agent therapeutically effective for the treatment or prevention of neurodegenerative disorders in mammals together with instructions to use the pharmaceutical agent in the treatment or prevention of neurodegenerative disorders in mammals. The pharmaceutical agent comprised in the commercial package is a propargylamine derivative or a pharmaceutically effective salt thereof corresponding to the compounds of formulae III or IV referred to previously. If required, the pharmaceutical agent is admixed with a pharmaceutically acceptable carrier, excipient or adjuvant.

Also within the scope of the present invention is a process for preparing a compound having the following formula III:

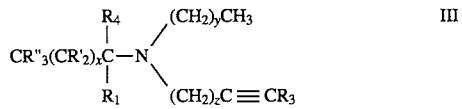

wherein

R', R", $R_1$, $R_3$, $R_4$, x, y and z are as defined previously.

The process comprises condensing an alkyl bromide with N-methylpropargylamine in the presence of a base and recovering the desired compound.

BRIEF DESCRIPTION OF THE DRAWINGS

FIG. 1 represents the stereospecific effect of N-(2-butyl)-N-methylpropargylamine.HCl on MAO-B inhibition. The inhibitory activity of R(−)[○] and S(+)[△] enantiomers as well as the racemic mixtures [↔] of 2-BuMP on rat liver mitochondrial MAO-B activities towards substrate 2-phenylethylamine ($1.9 \times 10^{-5}$M) was estimated. Results are of triplicate experiments.

The present invention will be more readily illustrated by referring to the following description.

DETAILED DESCRIPTION OF THE INVENTION

The present invention relates to the use of a class of propargylamines for the inhibition of MAO-B in vivo and in the prevention and treatment of premature degeneration of neuron cells in mammals. In its broadest aspect, the class of propargylamines contemplated within the scope of the present invention includes compounds falling within the following formula III:

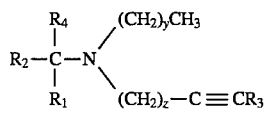

wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkythio or alkyl sulphinyl group having from 3 to 11 carbon atoms. $R_2$ is unsubstituted or substituted with at least one of the substituents selected from hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from O, S and/or N, and pharmaceutically acceptable salts thereof, in admixture with a pharmaceutically acceptable carrier, excipient or adjuvant.

In the case of MAO-B inhibition, it seems to be preferred that y be 0 and z be 1 and $R_3$ be hydrogen. It would appear that the presence of a methyl group on the right-hand side of the nitrogen atom is important in order for the overall compound to possess MAO-B inhibiting activities. Compounds where the —$(CH_2)_yCH_3$ group was replaced by a hydrogen atom or where y was equal to 1 were synthesized and tested for MAO-B inhibitory activity. In both cases, no substantial MAO-B inhibitory activity was observed. Also, it appears that the triple bond present on the propargyl moiety of the compound of formula III should be conjugated with nitrogen in order to yield compounds having optimal MAO-B inhibitory activity. Attempts to use compounds where z was equal to 2 did not yield compounds with substantial MAO-B inhibitory properties. However, this may not necessarily be a requirement when synthesizing compounds with neuroprotective properties not involving MAO-B inhibition.

There seems to be a minimum requirement that the straight or branched chain formed by the linking of substituent $R_2$ to the carbon atom adjacent the nitrogen atom on the compound of formula III be at least 4 carbon atoms in length. Compounds having unsubstituted aliphatic chains having less than 4 carbon atoms have shown marginal MAO-B inhibitory activities. With regard to the possible effect of double or triple bonds present on $R_2$ on the overall activity of the complete molecule, they are likely to be less influential than the length of the carbon chain itself. However, the conjugation of a double or triple bond on the left-hand side of the molecule with the nitrogen atom may have a deleterious effect on the overall activity of the molecule because this may cause a weaker effect of conjugation between the triple bond on the right-hand side of the molecule and the nitrogen atom.

The presence of functional groups on substituent $R_2$ is optional. Functional groups can have a positive influence on the overall MAO-B inhibitory or neuroprotective activities of the compound of formula III. In the case of MAO-B inhibition, however, the functional group on the last carbon atom of the longest segment of substituent $R_2$ should preferably be other than a carboxyl group or an ester group. These groups appear to render the molecule inactive, at least as far as MAO-B inhibition is concerned. Further characteristics of the compounds of the present invention will become more apparent by referring to the following description and examples.

Synthesis of the compounds

The compounds used in the context of the present invention can be prepared by condensing the appropriate alkyl bromides with N-methylpropargylamine in the presence of a base. Preferably, the base can be either an extra equivalent of N-methylpropargylamine or anhydrous sodium carbonate according to the following reaction schemes.

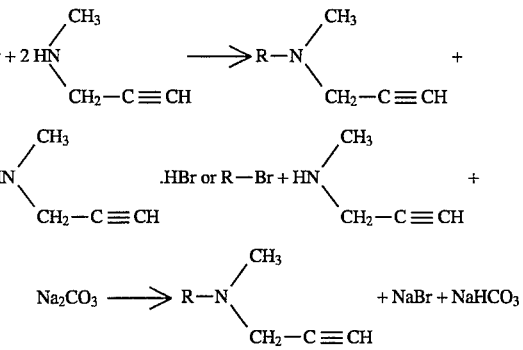

The former reaction is more convenient but more expensive. Any unreacted N-methylpropargylamine (b.p. 82°–84° C.) is readily removed during distillation of the solvent and in the water wash (solubility in water is infinite). The reaction can be carried out in ethanol, methanol, acetone, toluene, benzene or any solvent possessing similar properties, especially with regard to convenience of removal, evaporation and the like. Satisfactory yields were obtained when absolute ethanol was used. Hence, one of the interesting advantages of this method resides in the fact that methylpropargylamine has a low boiling point and is therefore easy to remove. Also, N-methylpropargylamine is soluble in water and therefore the clean-up is relatively simple.

The yields of the propyl, butyl and pentyl analogs are relatively low due to the volatility of the free bases (some loss occurs during removal of solvent) and to their slight to moderate solubility in water (further loss occurs during the water wash to remove N-methylpropargylamine hydrobromide and excess free base N-methylpropargylamine).

Alternatively, the compounds of the present invention can be prepared following the general procedure described in French Patent 1453844, issued Aug. 22, 1966 or in Boissier et al. (1966), Chimie Therapeutique, 320–326, which are hereby incorporated by reference. Finally and preferably, the compounds can also be prepared starting from a 2-aminoalkane, which is methylated via reaction with methyl chloroformate followed by reduction of the resulting carbamate with lithium aluminium hydride in ether. Without isolation of the N-methylalkylamine from the final ether solution, reaction with propargyl bromide with sodium carbonate as a base yields the desired N-2-alkyl-N-methylpropargylamine, isolated as its salt, preferably the hydrochloride or oxalate salt.

As mentioned previously, it can be desirable to prepare a specific isomeric form of one of the compounds of the present invention, as particular positional isomers and enantiomers have been shown to possess even more potent MAO-B inhibitory activity than their corresponding racemic mixtures. For example, in the case of positional isomers, the 2-alkyl propargylamine appears to be consistently more potent than the 1-alkyl propargylamine when the propargylamine has as a substituent a substituted or unsubstituted linear or branched aliphatic chain having between 7 and 13 carbon atoms. For propargylamines having a substituted or unsubstituted, linear or branched aliphatic chain having between 1 and 5 carbon atoms, the 1-alkyl propargylamine appears to be more selective toward MAO-B than toward MAO-A.

With regard to enantiomers, the R-(−)-enantiomer appears to be considerably more active functionally than the S-(+)-enantiomer in the inhibition of MAO-B activity and more generally in the prevention and treatment of neurodegenerative disorders. It is thus the enantiomer of interest.

As an illustrative example, (+) or (−)-2-butylamine is reacted with methylchloroformate and the resulting product (a carbamate) is reduced with lithium aluminum hydride to produce (+) or (−) N-methyl-2-butylamine. The formed methyl compound, still in the ether solution from the previous step, can then be directly reacted with propargyl bromide and sodium carbonate without requiring previous isolation or purification. The final ethereal reaction mixture is then filtered and washed with water to remove the remaining reagents and then dried. The desired compound, which is still dissolved in ether, is then added to a suitable acid such as oxalic acid to yield the final product as a salt which can be recrystallized from a solvent or solvent mixture such as methanol/ether if required. Any competent chemist will appreciate that any reagent used in this process may be replaced by another compound performing the same function.

HCl salts can be prepared for all members of the series following procedures which are well-known to those skilled in synthetic chemistry. In the case of the propyl, butyl and pentyl analogs, the HCl salts appear to be difficult to re-crystallize but the oxalate salts, which crystallize readily, can be alternatively prepared. Recrystallization of the HCl salt proceeded more satisfactorily from acetone/hexane than from methanol/ether (see example 11 for specific details). With regard to the hydrochlorides of the longer alkyl chain analogs, they crystallized without difficulty. It is to be understood by the skilled chemist that salts such as sulphates, tartrates, benzoates, hydrobromides and the like can also be prepared. In fact, the appropriate choice of the type of salt may be useful to impart further advantages to the analogs of the present invention such as lowering solubility or causing slower release.

Structural identity of the described compounds can be ascertained by mass spectrometry and elemental analysis. The mass spectra of all the compounds are characterized by a small molecular ion (typically less than 10% relative intensity) and a base peak (relative intensity 100%) arising by bond cleavage of the alkyl chain alpha to the nitrogen atom.

Synthesis of preferred compounds of the present invention will be more readily illustrated by referring to the following examples.

EXAMPLE 1

N-Methylpropargylamine-HCl (MP).

N-methylpropargylamine (Aldrich Chemical Co., Milwaukee, U.S.A.) (1.0 g, 14 mmol) in dry ether (75 mL) was treated with a solution of ethanolic hydrochloric acid (prepared by the addition of 3.5 mL acetyl chloride to 35 mL of ice-cold absolute ethanol) until the precipitation of white solid ceased. The precipitate was filtered and recrystallized from ethanol/ether. The yield of white crystals was 1.25 g (85%), m.p. =105°–106° C.

EXAMPLE 2

N-Methyl-N-(2-propyl)propargylamine hydrochloride (2-PrMP).

2-Bromopropane (3.08 g, 25 mmoles) and N-methylpropargylamine (3.45 g, 50 mmoles) in absolute ethanol (50 mL) were heated at reflux for 48 h. The free base was isolated in ether as described for Example 3 below. On treatment of the dried ether solution of the free base with ethanolic hydrochloric acid, at first an oil separated and then white needles (m.p. 155°–156° C.) subsequently precipitated very slowly from the supernatant (white needles, recrystallized from methanol-ether). The oil and the needles gave identical mass spectra.

Elemental analysis: $C_{17}H_{14}ClN$; Calculated: C=56.94%, H=9.56%, N=9.49%; Found: C=57.07%, H 9.63%, N=9.52%; Mass spectrum: $M^+$=111 (10%), base peak m/e= 96.

EXAMPLE 3

N-(2-Butyl)-N-methylpropargylamine hydrochloride and oxalate (2-BuMPP).

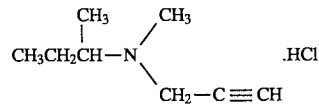

A solution of 2-bromobutane (6.86 g, 50 mmoles) in absolute ethanol (5 mL) was added to a gently refluxing solution of N-methylpropargylamine (3.46 g, 50 mmoles) in absolute ethanol (45 mL) containing powdered anhydrous sodium carbonate (5.3 g, 50 mmoles). After stirring under gentle reflux for 72 h, the mixture was allowed to cool, then was filtered and 45 mL of ethanol was distilled off. The residue was diluted with 75 ml of ethyl ether and washed with 2×20 mL water. The ethereal solution was dried over anhydrous magnesium sulfate and filtered. The filtrate was then diluted to 150 mL with ether and treated with ethanolic hydrochloric acid (prepared by the addition of 50 mmoles of acetyl chloride to 10 mL of ice-cold absolute ethanol). The initial, rapid precipitation was an oil which very slowly crystallized; white needles subsequently very slowly precipitated from the supernatant. Overall yield was 35%, m.p. 150°–151° C.:.

Elemental analysis: $C_8H_{16}ClN$: Calculated: C=59.43% H=9.98% N=8.66% Found: C=59.60% H=10.11% N=8.51% Mass spectrum: $M^+$=125 (4%), base peak m/e=96, M—$CH_3$=m/e 110 (15%).

The oxalate salt was readily formed by the addition of the ethereal solution of the free base (prepared as described above) to a stirred solution of oxalic acid (4.5 g, 50 mmoles) in anhydrous ether (500 mL). Yield was 34%, m.p. 123°–124° C.:

Elemental analysis: $C_{10}H_{17}N_4$: Calculated: C=55.80% H=7.96% N=6.51% Found: C=55.93% H=7.86% N=6.64%.

Similar yields of the title compound were obtained when an extra 50 mmoles of N-methylpropargylamine were used as base instead of anhydrous sodium carbonate.

EXAMPLE 4

Alternate method for the preparation of N-(2-butyl)-N-methylpropargylamine oxalate.

A solution of 2-aminobutane (5.0 g, 68 mmoles), 4-dimethylaminopyridine (850 mg, 7mmoles) and triethylamine (8.4 g, 83 mmoles) in dichloromethane (150 mL) was cooled in an ice-water bath and treated drop-wise with methyl chloroformate (7.05 g, 75 mmoles). After one hour, the reaction mixture was diluted with dichloro- methane (150 mL) and washed successively with water (80 mL), 0.1N HCl (2×80 mL) and water (80 mL), then dried over anhydrous sodium sulfate. Removal of the solvent gave 9.0 g (100%) of product as a pale yellow oil which was reduced by addition to a suspension of lithium aluminum hydride (3.6 g, 95 mmoles) in ether (185 mL). Following gentle reflux for two hours, the product was isolated in ether by the careful addition of water (3.6 mL), 10% NaOH (3.6 mL) and water (10 mL) and filtration. The ether solution was dried over anhydrous magnesium sulfate then treated with propargyl bromide (8.1 g, 68 mmoles) and sodium carbonate (7.2 g, 68 mmoles). The mixture was gently refluxed for 24 hours, then filtered. The product was isolated as the oxalate salt by addition of the filtrate to a stirred solution of oxalic acid (6.1 g, 68 mmoles) in ether (250 mL). The precipitate was filtered with suction and dried (6.0 g) (41% overall yield). (m.p.= 124°–125° C.).

This procedure can be used to prepare the two stereoisomers of the product since (R)-2-aminobutane and (S)-2-aminobutane are commercially available. (R)(−)-N-(2-Butyl)-N-methylpropargylamine oxalate [R-(−)2-BuMP].

A solution of (R)-(−)-sec-butylamine (Aldrich Chemical Co., 4.86 g, 67mmol, [alpha]$^{19}$−7.5° neat) in dichloromethane (150 mL) containing triethylamine (8.4 g, 83 mmol) and 4-dimethylaminopyridine (859 mg, 7 mmol) was cooled in an ice-water bath and treated with methylchloroformate (7.05 g, 75 mmol). After stirring for 2 hours, the solution was diluted with an equal volume of dichloromethane and washed successively with water (80 mL), 0.1N hydrochloric acid (2×80 mL) and water (80 mL). After drying over anhydrous magnesium sulfate, the solution was rotary evaporated to dryness to give the carbamate in 100% yield. This was reduced by adding an ethereal solution of it to a stirred suspension of lithium aluminum hydride (3.6 g, 95 mmol) in ether (185 mL). The mixture was stirred at 30° C. for 3 h, then treated successively with water (3.6 mL), 10% sodium hydroxide (3.6 mL) and water (10 mL) and stirred for another hour. Following filtration of the lithium and aluminum salts, the filtrate was dried over anhydrous magnesium sulfate and filtered again. To the dried filtrate was added sodium carbonate (7.2 g, 68 mmol) and propargyl bromide (8.1 g, 68 mmol). The mixture was stirred under reflux for 48 hours, allowed to cool and filtered. The filtrate was washed with water (2×75 mL), dried, filtered and added slowly to a stirred solution of oxalic acid (6.0 g, 67 mmol) in ether (250 mL). The precipitate was filtered with suction and washed well with ether. Yield=9.7 g (67%). The product was recrystallized from methanol/ether to give 8.2 g of white crystals, m.p.=102°–104° C. Neither of the above reactions involves the optically active center; the product will, therefore, be as optically pure as the starting material. Elemental analysis: $C_{10}H_{17}NO_4$: Calculated: C=55.90%, H=7.96%, N=6.51%; Found: C=55.89%, H=8.13%, N=6.27%; Mass spectrum {m/e (relative intensity)}: M$^+$=125 (10%); [M—CH$_3$]=110 (20%); [M—{CH$_2$CH$_3$}]=96 (100%).]

EXAMPLE 6

(S)(+)-N-(2-Butyl)-N-methylpropargylamine oxalate [S(+)2-BuMP].

The procedure follows exactly that of the (R) enantiomer described in Example 5, starting with (S)-(+)-sec-butylamine (Aldrich Chemical Co., 4.75 g, mmol, [alpha]$^{19}$+7.5° neat). The product was obtained as the oxalate salt in a yield 9.95 g (71%) and was recrystallized from methanol/ether. m.p.=118°–0° C.

Elemental analysis: $C_{10}H_{17}NO_4$: Calculated: C=55.80%, H=7.96%, N=6.51%; Found: C=55.72%, H=7.85%, N=6.24%; Mass spectrum {m/e (relative intensity)}: M$^+$—CH$_3$ (11%); [M—(CH$_2$CH$_3$)]=96 (100%).]

EXAMPLES 7–15 and 17–20.

The process used in Example 3 was also used for the preparation of the compounds described in Examples 7–15 and 17–20. However, where methylpropargylamine base or Na2CO$_3$ are used, it is important if using Na$_2$CO$_3$ to filter it off before continuing the synthesis. This is not a problem when using N-methylpropargylamine although in this case, it is necessary to wash away the excess reagent with water.

EXAMPLE 7

N-(1-Butyl)-N-methylpropargylamine hydrochloride (1-BuMP)

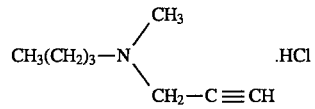

1-Bromobutane (6.86 g, 50 mmoles), N-methylpropargylamine (3.46 g, 50 mmoles) and anhydrous sodium carbonate (5.3 g, 50m moles) heated for 72 h. in absolute ethanol gave a 52% yield of the title compound after recrystallization from methanol-ether, m.p.=144°–145° C. The same compound in approximately the same yield was obtained when 1-bromobutane (50 mmoles) and N-methylpropargylamine (100 mmoles) were gently refluxed for 72 h. in absolute ethanol.

Elemental analysis: $C_8H_{16}ClN$: Calculated: C=59.43% H=9.98% N=8.66% Found: C=59.69% H=9.94% N=8.77% Mass spectrum: M$^+$=125 (4%), base peak m/e= 82, M-CH$_3$= m/e 110 (8%).

EXAMPLE 8

N-(1-Pentyl)-N-methylpropargylamine oxalate (M-1-PP).

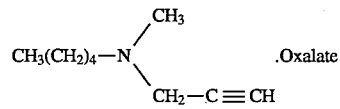

1-Bromopentane (12.1 g, 80 mmoles) and N-methylpropargylamine (11.1 g, 160mmoles) were refluxed in absolute ethanol (75 mL) for 72 h. to give (after addition to 80 mmoles of oxalic acid in ether) the title compound in 60% yield after recrystallization from methanol-ether, m.p.= 101°–103° C.

Elemental analysis: $C_{11}H_{19}NO_4$: Calculated: C=57.63% H=8.35% N=6.11% Found: C=57.72% H=8.29% N=5.92% Mass spectrum: $M^+$=139 (3%), base peak m/e= 82.

EXAMPLE 9

N-(2-Pentyl)-N-methylpropargylamine hydrochloride and oxalate (M-2-PP).

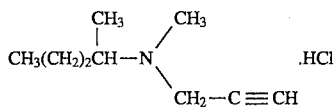

2-Bromopentane (12.1 g, 80 mmoles) and N-methylpropargylamine (11.1 g, 160 mmoles) were heated at reflux for 48 h. in absolute ethanol (50 mL). The hydrochloride salt precipitated from ether as white solid (m.p. 94°–95° C.) which did not crystallize (yield =63%).

Elemental analysis: $C_{11}H_{18}ClN$: Calculated: C=61.52%, H=10.33%, N=7.97% Found: C=61.05%, H=10.47%, N=8.20% Mass spectrum: $M^+$=139 (6%), base peak=m/e 96, M—$CH_3$=m/e 124 (21%).

The oxalate salt (yield 50%), from free base prepared as above, was recrystallized from methanol-ether, m.p. 89°–90° C.

Elemental analysis: $C_{11}H_{19}NO_4$: Calculated: C=57.63% H=8.35% N=6.11% Found: C=57.58% H=8.22% N=6.01% Mass spectrum: $M^+$=139 (4%), base peak=m/e 96, M—$CH_3$=124 (22%).

EXAMPLE 10

N-Methyl-N-(3-pentyl)propargylamine oxalate (M-3-PP).

A mixture of 3-bromopentane (7.55 g, 50 mmol), N-methylpropargylamine (3.46 g, 50 mmol) and anhydrous sodium carbonate (5.3 g, 50 mmol) in acetone (50 mL) was refluxed with stirring for 7 days. After allowing to cool, the mixture was filtered and most of the acetone was distilled off. The residue was taken up in ether (75 mL) and washed with water (2×25 mL). The ether solution was dried over magnesium sulfate and then added to an ether solution of oxalic acid (4.5 g). The crude product was recrystallized from methanol/ether to give 1.0 g of pale brown crystals (m.p. 104°–105° C.).

Elemental analysis: $C_{11}H_{19}NO_4$: Calculated: C=57.63%, H=8.35%; Found: C=58.85%, H=8.46%; Mass spectrum {m/e (relative intensity)}: $M^+$= 139 (4%); [M—($CH_2CH_3$)] =110 (100%).]

EXAMPLE 11

N-(2-Hexyl)-N-methylpropargylamine hydrochloride (2-HxMP).

2-bromohexane was prepared from 2-hexanol by reaction with thionyl chloride/thionyl bromide in a manner similar to that described by Frazier etal. (Chem. Ind. (1954), 931–932) hereby incorporated by reference, for the preparation of 2-bromobutane from 2-butanol.

2-bromohexane (16.5 g, 100 mmol), N-methylpropargylamine (6.92 g, 100 mmol) and anhydrous sodium carbonate (10.6 g, 100 mmol) were refluxed in absolute ethanol (125 mL) for 7 days. The cool reaction mixture was filtered and most of the ethanol distilled. The residue was taken up in ether (150 mL) and washed with water (2×50 mL). After drying the ether solution over magnesium sulfate, sufficient ethanolic hydrochloric acid was added to convert all the product to its hydrochloride salt (which did not precipitate).

Rotary evaporation of the resulting solution gave 12 g (63%) of a dark brown, very viscous liquid which was decolorized by boiling with activated charcoal in acetone. The pale brown acetone filtrate (200 mL) was treated with hexane until the solution became cloudy (200 mL required). A viscous oil precipitated. The supernatant was decanted and hexane (50 mL) added to give again a cloudy solution. Again a viscous oil precipitated. This process was repeated several times until the supernatant no longer became cloudy on the addition of more hexane. The first two or three viscous oil precipitates would not crystallize, the next few crystallized on air drying and standing, while the later precipitations were as white crystals (m.p. 98°–99° C.). Elemental analysis: $C_{10}H_{20}ClN$: Calculated: C=63.31%, H=10.63%; Found: C=63.24%, H=11.06%; Mass spectrum: $M^+$=153 (2%), [M—$CH_3$]=138 (10%), [M—$C_4H_9$]=96 (100%).]

EXAMPLE 12

N-(1-Heptyl)-N-methylpropargylamine hydrochloride (1-HMP).

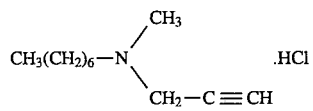

1-Bromoheptane (3.58 g, 20 mmoles) and N-methylpropargylamine (2.76 g, 40 mmoles) were refluxed in absolute ethanol for 24 h. The product separated immediately on treatment with ethanolic HCl as mediumbrown crystals in a yield of 100% (84% as white crystals after recrystallization from methanol-ether), m.p.=124°–125° C.

Elemental analysis: $C_{11}H_{22}ClN$: Calculated: C=64.84% H=10.88% N=6.87% Found: C=64.97% H=10.78% N=6.92% Mass spectrum: $M^+$=167 (18%), base peak=m/e 82, M–[C—CH]=m/e 142 (15%).

EXAMPLE 13

N-(2-Heptyl)-N-methylpropargylamine hydrochloride (2-HMP).

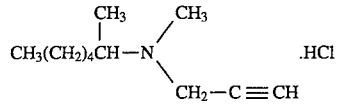

2-Bromoheptane (7.16 g, 40 mmoles) and N-methylpropargylamine (5.52 g, 80 mmoles) were gently refluxed for 24 h. in absolute ethanol (50 mL). Yield was 100% (66% after recrystallization from acetonepentane), m.p.=115°–116° C.

Elemental analysis: $C_{11}H_{22}ClN$: Calculated: C=64.84% H=10.88% N=6.87% Found: C=65.01% H=10.93% N=6.95% Mass spectrum: $M^+$=167 (5%), base peak=m/e 96, M-$CH_3$ (23%).

EXAMPLE 14

N-(2-Decyl)-N-methylpropargylamine hydrochloride (2-DMP).

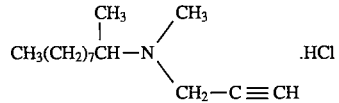

2-Bromodecane (8.84 g, 40 mmoles) and N-methylpropargylamine (5.52 g, 80 mmoles) were heated in absolute ethanol (50 mL) for 72 h. to give, after treatment with 40 mmoles of ethanolic hydrochloric acid, the title compound in a yield of 100% (75% after recrystallization from methanol-ether), m.p.=130°–131° C.

Elemental analysis: $C_{14}H_{28}ClN$: Calculated: C=68.40% H=11.48% N=5.70% Found: C=68.20% H=11.36% N=5.82% Mass spectrum: $M^+$=209 (1%), base peak=m/e 96, M—$CH_3$ (33%).

EXAMPLE 15

(2-Dodecyl)-N-methylpropargylamine hydrochloride (2-DfMP).

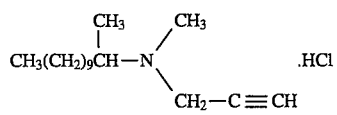

2-Bromododecane (5.3 g, 21 mmoles) and N-methylpropargylamine (3.45 g, 50 mmoles) were heated at reflux in absolute ethanol (50 mL) for 48 h. After treatment of the free base with ethanolic hydrochloric acid, the title compound was obtained in a yield of 30% after recrystallization from acetone-pentane, m.p.=128°–130° C.

Elemental analysis: $C_{16}H_{32}ClN$: Calculated: C=70.16% H=11.78% N=5.12% Found: C=70.28% H=11.80% N=5.03% Mass spectrum: $M^+$=237 (0.05%), base peak= m/e 96, M—$CH_3$=m/e 222 (10%).

EXAMPLE 16

N-(4-Chloro-1-butyl)-N-methylpropargylamine-HCl (Cl-1-BuMP).

4-chlorobutyronitrile (25 g, 243 mmol) in dry ether (25 mL) was added to a stirred suspension of lithium aluminum hydride (11.4 g, 300 mmol) in dry ether (500 mL). After stirring for 12 h at 20° C., water (11.4 mL), 10% sodium hydroxide (11.4 mL) and finally water (33 mL) were very slowly added. Stirring was continued for another hour, the mixture was filtered and the filtrate was dried over anhydrous magnesium sulfate. The product (4-chloro-1-aminobutane) was not isolated. To the ethereal solution was added triethylamine (31.5 g, 312 mmol) and 4-dimethylaminopyridine (2.5 g). To this cooled, stirred solution was added methyl chloroformate (26.3 g, 280 mmol). After stirring at 20° C. for 12 h, the mixture was filtered from the precipitated triethylamine hydrochloride and the filtrate was washed successively with water (2× 150 mL), 0.1N hydrochloric acid (2×150 mL) and water (150 mL). The organic layer was dried over anhydrous magnesium sulfate, filtered and then added slowly to a stirred suspension of lithium aluminum hydride (14 g, 368 mmol) in ether (500 mL). After stirring at 20° C. for 16 h, the solution was treated carefully with water (14 mL), 10% sodium hydroxide (14 mL), and water (42 mL), then stirred for 1 h before filtering. The filtrate was dried over anhydrous magnesium sulfate. Without isolating the product [N-(4-chloro-1-butyl)methylamine], anhydrous sodium carbonate (25.8 g, 243 mmol) and propargyl bromide (28.9 g, 243 mmol) were added and the solution was gently refluxed with stirring for four days. After filtration and drying over magnesium sulfate, the ethereal solution of crude title compound was treated with ethanolic hydrochloric acid. A colorless oil precipitated which could not be successfully crystallized. The yield was 3.6 g (10% overall). The mass spectrum showed no molecular ion, but did exhibit as base peak m/e 82 arising from cleavage of the butyl chain alpha to the nitrogen atom.

EXAMPLE 17

N-(3-Carboxy-1-propyl)-N-methylproparglamine oxalate (3-CP-MP).

A mixture of ethyl 4-bromobutyrate (19.5 g, 100 mmol), N-methylpropargylamine (6.92 g, 100 mmol) and anhydrous sodium carbonate (10.6 g, 100 mmol) was refluxed with stirring in 115 mL of absolute ethanol for 7 days. After allowing to cool, the mixture was filtered and the filtrate was rotary evaporated to dryness. The residue was taken up in ether (150 mL), washed with water (3×50mL), dried over magnesium sulfate and the solvent removed by rotary evaporation to give 14.2 g (78%) of a viscous liquid which was used without further purification. The viscous liquid was treated with a solution of potassium hydroxide (7.0 g) in tert-butanol (125 mL) and stirred at 20° C. for 20 hours. The solution was evaporated to dryness and the residue was taken up in water (100 mL), then neutralized to pH 6.5–7.0 with hydrochloric acid and rotary evaporated to dryness again. The semi-solid residue was allowed to dry further by leaving uncovered for 48 hours, and then was triturated in ice-cold methanol and filtered immediately from the nearly insoluble potassium chloride. The filtrate was rotary evaporated at 30° C. to give 12.8 g of a brownish viscous liquid (83%), the mass spectrum of which revealed it to be the title compound as the free base. The oxalate salt was prepared by dissolving the product (3.64 g, 23 mmol) in methanol (15 mL) and adding to a solution of oxalic acid in methanol (25 mL) and then diluting with 300 mL ether. The oxalate was a viscous liquid which crystallized with difficulty. It was recrystallized from methanol/ethyl acetate to give white plates (m.p. 73°–75° C.). [Mass spectrum: $M^+$=155 (2%); [M—(C≡CH)]=130 (3%); [M—(HOOC–$CH_2CH_2$)]=82 (00%).]

EXAMPLE 18

N-(5-Carbethoxy-2-pentyl)-N-methylpropargylamine-HCl(5-CP2MP).

Ethyl 4-acetylbutyrate was prepared by esterification of 4-acetylbutyric acid (Aldrich Chemical Co.). Selective reduction of the ketone to the secondary alcohol was achieved by the dropwise addition of a solution of sodium borohydride (4.94 g, 130 mmol) in dilute sodium hydroxide (preParedby diluting 7 mL of 10% sodiumhydroxide with 63 mL water) to an ice-cold, stirred solution of the above ester (53.65 g, 340 mmol) in methanol (350 mL). After stirring at 20° C. for 16 hours, most of the methanol was removed by rotary evaporation at 40° C. The cold residue was diluted with cold water (350 mL) and then extracted immediately with ether (3×150 mL). After drying over anhydrous magnesium sulfate, the ether was evaporated to give the reduced product, a hydroxy ester, as a pale yellow liquid in 60% yield. Treatment of a chloroform solution (500 mL) of the hydroxy ester (31.8 g, 200 mmol) with bromotrimethylsilane (61.2 g, 400 mmol) at 50° C. for 27 hours, followed by washing of the cold reaction mixture with 5% sodium bicarbonate (2×150 mL), drying over anhydrous sodium sulfate and rotary evaporation of the solvent at 35° C. gave ethyl 5-bromohexanoate.

A solution of ethyl 5-bromohexanoate (38.8 g, 188 mmol), N-methylpropargylamine (13.0 g, 188 mmol) and anhydrous sodium carbonate (20 g, 190 mmol) in 250 mL absolute ethanol was stirred under reflux for 6 days. The cooled reaction mixture was filtered with suction and then rotary evaporated to dryness at 45° C. The residue was taken up in ether (150 mL) and washed with water (3×50 mL). The ether layer was dried over magnesium sulfate, filtered and rotary evaporated to give 9.6 g of a brownish viscous oil. The hydrochloride salt was prepared by the addition of ethanolic hydrochloric acid to an ethereal solution of the free base (m.p. 113° C.).

Elemental analysis: $C_{12}H_{22}ClNO_2$: Calculated: C=58.17% H=8.95% N=5.65%; Found: C=56.63%, H=8.74%, N=5.69%; Mass spectrum: $M^+$=211 (0.5%), M=$CH_3$=196 (15%), [M—($OCH_2CH_3$)]=166 (30%), [M—($CH_2CH_2CH_2COOCH_2CH_3$)]=96 (100%).]

EXAMPLE 19

N-(5-carbethoxy-1-pentyl)-N-methylpropargylamine oxalate (5-CP1MP).

A mixture of ethyl-6-bromohexanoate (25.2 g, 112 mmol) (Aldrich Chem. Co. Milwaukee), N-methylpropargylamine (7.74 g, 112 mmol) and anhydrous sodium carbonate (11.9 g, 112 mmol) was refluxed with stirring in absolute ethanol (115 mL) for 7 days. After filtration and rotary evaporation, the residue was taken up in ether (150 mL) and washed with water (3×50 mL). The ether solution was dried over magnesium sulfate, filtered and rotary evaporated to give 16.8 of a brownish viscous oil. The oxalate salt was prepared as a white crystalline solid (m.p. 74°–77° C.) by the addition of an ethereal solution of the title compound to an ether solution of oxalic acid.

Elemental analysis: $C_{14}H_{23}N_{06}$: Calculated: C=55.80%, H=7.69%, N=4.65%; Found: C=56.22%, H=8.13%, N=4.39%; Mass spectrum: $M^+$=211 (0.5%), [M—($OCH_2CH_3$)]=166 (35%), [M—($COOCH_2CH_3$)]=138 (8%), [M—($CH_2COOCH_2CH_3$)]=124 (6%), [M—($CH_2CH_2COOCH_2CH_3$)]=110 (6%), [M—($CH_2CH_2COOCH_2CH_3$)]=110 (6% ), [M—($CH_2CH_2CH_2$ $COOCH_2$—$CH_3$)]=96 (8% ), [M—($CH_2CH_2CH_2CH_2COOCH_2CH_3$)]=82 (100%).]

EXAMPLE 20

N-(6-Hydroxy-1-hexyl)-N-methylpropargylamine-HCl (6-OH-Hx1MP).

N-(5-Carbethoxy-1-pentyl)-N-methylpropargylamine (as prepared above, 10.6 g, 50 mmol) was dissolved in t-butanol (200 mL) and powdered sodium borohydride (4.75 g, 125 mmol) was added. The solution was stirred, brought to a gentle reflux and treated very slowly (over 45 min) with methanol (40 mL, 1 mole). After stirring for another hour under reflux, the solution was allowed to cool and then the reaction was quenched with water (90 mL). Most of the methanol and t-butanol were removed by rotary evaporation leaving an aqueous residue which was extracted with chloroform (75 mL). After drying over anhydrous sodium sulfate, the chloroform solution was rotary evaporated to give 7.6 g (90%) of crude title compound. The mass spectrum exhibited no molecular ion, but a mass of m/e 82 (due to cleavage alpha to the nitrogen atom) was the base peak. No masses due to starting material or to reduction of the propargyl group were present.

EXAMPLE 21

N-(2-Butyl)-N-ethylpropargylamine hydrochloric salt [2-BuEP].

N-Ethyl-2-butylamine was prepared by the condensation of 2-butylamine (29.2 g, 400 mmol) with acetaldehyde (26.4 g, 600 mmol) in ether (500 mL) to which anhydrous magnesium sulfate was added. After stirring at 20° C. for 4 days, the mixture was filtered, the filtrate concentrated to about 125 mL and then added slowly to a stirred suspension of lithium aluminum hydride (9.0 g, 237 mmol). After stirring at 20° C. for 6 hours, the salts were decomposed by the dropwise addition of water (9 mL), 10% sodium hydroxide (9 mL) and water (27 mL). After stirring for 1 hour, the mixture was filtered, the ether was distilled from the filtrate and the residue distilled at atmospheric pressure to give N-ethyl-2-butylamine (b.p.=99°–102° C.). The product (5.5 g, 40 mmol), propargyl bromide (4.76 g, 40 mmol), and anhydrous sodium carbonate (4.24 g, 40 mmol) in acetone (50 mL) were stirred under gentle reflux for 3 days. The product was isolated as the hydrochloride salt which separated as a colorless viscous oil. The mass spectrum was correct for the title compound ($M^+$=m/e 139 (5%); M—$CH_3$=m/e 124 (13%); base-peak=m/e 110).

EXAMPLE 22

N-(1-Butyl)-N-ethylpropargylamine oxalate salt [1-BuEP].

N-Ethyl-1-aminobutane (Aldrich Chemical Co.)(5.05 g, 50 mmoles), anhydrous sodium carbonate (5.3 g, 50 mmoles) and propargyl bromide (5.95 g, 50 mmoles) were combined in dry ether (150 mL) and stirred under gentle reflux for 48 hours. After filtration of the cold reaction mixture, the filtrate was washed with water (2×75 mL), dried over magnesium sulfate and again filtered. Treatment with ethanolic hydrochloric acid gave a copious white precipitate which proved to be hygroscopic (dry weight=8.3 g, 94%). The free base was regenerated, dissolved in ether and added to an ethereal solution of oxalic acid. The heavy offwhite precipitate was filtered and air-dried (yield= 7.9 g), then recrystallized from methanol-ether, m.p. =83°–84° C.

Elemental analysis: $C_{11}H_{19}NO_4$: Calculated: C=57.63%, H=8.35%, N=6.11%; Found: C=58.08%, H=8.29%, N=5.54%;

Mass spectrum: $M^+$=139 (20%); [M—($CH_2CH_2CH_3$)]= 96 (100%); M—$CH_3$=124 (15%).

EXAMPLE 23

N-(2-Butyl)propargylamine hydrochloride salt (2-BuEP).

A mixture of 2-butylamine (14.6 g, 200 mmol), propargyl bromide (23.8 g, 200 mmol) and anhydrous sodium carbonate (21.1 g, 200 mmol) in dry ether (400 mL) was gently refluxed for 24 h. After filtration, the ether and unreacted 2-butylamine were removed by rotary evaporation and the residue distilled at 25 mm. The fraction distilling at 115°–120° C. was converted to its hydrochloride salt, m.p.= 87°–88° C. The mass spectrum was correct for the title compound ($M^+$=m/e 111 (4%); M—$CH_3$=m/e 96 (35%); base peak= m/e 82).

EXAMPLE 24

N-(3-Butynyl)-N-(2-butyl)methylamine oxalate salt [3-BuBuM].

N-Methyl-2-aminobutane was prepared from 2-aminobutane (24.7 g, 333 mmol) by reaction with methyl chloroformate (29 mL, 375 mmol) in dichloromethane (700 mL) containing 4-dimethylaminopyridine (4.25 g, 35 mmol) and triethylamine (58.5 mL, 415 mmol). N-carbomethoxy-2-aminobutane was isolated in 100% yield following washing of the reaction solution with water and 0.1N hydrochloric acid, drying of the solvent over sodium sulfate and rotary evaporation of the solvent. An ethereal solution of the product was added dropwise to a stirred suspension of lithium aluminum hydride (19.0 g, 500 mmol) in ether (1 L). After destruction of the aluminum and lithium complexes by careful addition of water (10 mL), 10% sodium hydroxide (10 mL) and water (57 mL), the solids were filtered and the ether was distilled off at atmospheric pressure. The residue was distilled to give 14 g of N-methyl-2-aminobutane as a clear colorless liquid (b.p.=74°–76° C./720 mm).

3-Bromo-1-butyne was prepared from 3-butyn-1-ol (25 g, 357 mmol) by the method of Frazer et al. (M. J. Frazer, W. Ferrard, G. Machell and B. D. Shepperd, Chem. Ind. (1954) 931–932) using thionyl chloride and thionyl bromide. The product was distilled at atmospheric pressure (b.p.= 108°–110° C.).

N-Methyl-2-aminobutane (4.4 g, 50 mmol), anhydrous sodium carbonate (5.3 g, 50 mmol) and 3-bromo-1-butyne (6.65 g, 50 mmol) were stirred under reflux in acetone (50 mL) for 10 days. The cooled reaction mixture was filtered with suction and most of the acetone was distilled. The residue was taken up in ether (75 mL) and washed with water (2×25 mL). After drying over anhydrous magnesium sulfate, the ether solution was treated with ethanolic hydrochloric acid. A colorless, viscous oil precipitated which could not be crystallized. The free base was regenerated, dissolved in ether and added to an ether solution of oxalic acid to give a colorless viscous oil which crystallized on standing. The product was recrystallized from methanol/ether as white crystals, m p=96°–97° C. in a yield of 19 g Elemental analysis: $C_{11}H_{19}NO_4$: Calculated: C=57.63%, H=8.35%, N=6.11% Found: C=56.66%, H=8.71%, N=6.90% Mass spectrum: $M^+$=139 (18%); [M—($CH_2CH_3$)] =110 (17%), [M—($CH_2$-C≡CH)]=100 (60%).

MAO inhibition studies a) Inhibition of MAO activities in vitro.

A radioenzymatic procedure was used for the estimation of MAO activities (Neuromethods V; Neurotransmitter enzymes, 1986, Humana Press, N.J.). MAO-A and MAO-B activities from rat liver mitochondrial membranes were assayed using 5-HT ($5\times10^{-4}$M) and PE ($5\times10^{-5}$M) as substrates respectively. The aliphatic propargylamine inhibitors (from $1\times10^{-10}$M to $1\times10^{-4}$ M) were preincubated with the MAO for 20 min. at ambient room temperature and then the residual enzyme activities were determined by addition of the substrates, followed by further incubation at 37° C. for 30 min. The enzymatic reactions were terminated by the addition of citric acid and the aldehyde products were extracted with toluene: ethyl acetate (1:1, v/v) and the radio-activities assessed in a scintillation counter. The inhibitory activities ($IC_{50}$) of aliphatic propargylamines, towards MAO-B and MAO-A are summarized in Table 1. Most of them are highly selective MAO-B inhibitors with MAO-A/MAO-B ratios of their IC50 values ranging from 20 to 200. Compounds with longer carbon chain lengths are more active in the inhibition of MAOB activity in vitro and some of them are more selective than Deprenyl. These compounds also actively inhibit the deamination of dopamine (DA), which is a mixed-type MAO (A and B) substrate.

TABLE 1

Inhibition of rat liver monoamine oxidase activities towards different substrates by some aliphatic propargylamines in vitro

| Inhibitors* | PE ($1.9 \times 10^{-5}$M) $IC_{50}$ | 5-HT ($5 \times 10^{-4}$M) $IC_{50}$ | Ratio MAO-A/ MAO-B | DA ($5 \times 10^{-4}$M) $IC_{50}$ |
|---|---|---|---|---|
| MP | inactive | inactive | | inactive |
| 2-PrMP | $2 \times 10^{-5}$M | no effect | | $3 \times 10^{-5}$M |
| 1-BuMP | $1 \times 10^{-6}$M | $1 \times 10^{-4}$M | 100 | — |
| 2-BuMP | $1 \times 10^{-6}$M | $2 \times 10^{-5}$M | 20 | $5 \times 10^{-7}$M |
| M-1-PP | $4 \times 10^{-7}$M | $1 \times 10^{-4}$M | 200 | — |
| M-2-PP | $2 \times 10^{-7}$M | $1 \times 10^{-5}$M | 50 | $6 \times 10^{-6}$M |
| M-3-PP | $2 \times 10^{-7}$M | $2 \times 10^{-6}$M | 10 | — |
| 2-HxMP | $1 \times 10^{-7}$M | $1 \times 10^{-4}$M | 1000 | — |
| 1-HMP | $2 \times 10^{-6}$M | $4 \times 10^{-5}$M | 20 | — |
| 2-HMP | $2 \times 10^{-7}$M | $2 \times 10^{-5}$M | 100 | $3 \times 10^{-7}$M |
| 2-DMP | $2 \times 10^{-7}$M | $4 \times 10^{-6}$M | 50 | $2 \times 10^{-7}$M |
| 2-DdMP | $4 \times 10^{-8}$M | $2 \times 10^{-6}$M | 50 | $3 \times 10^{-7}$M |
| Cl-1-BuMP | $1 \times 10^{-5}$M | $>1 \times 10^{-4}$M | >10 | — |
| 3-CP-MP | inactive | inactive | | inactive |
| 5-CP2MP | inactive | inactive | | inactive |
| 5-CP1MP | inactive | inactive | | inactive |
| 6-OH-Hx1MP | $1 \times 10^{-4}$M | inactive | | — |
| 2-BuPP | inactive | inactive | | |
| 1-BuEP | inactive | inactive | | |
| 2-BuEP | inactive | inactive | | |
| 3-BuBuM | inactive | inactive | | |
| Deprenyl** | $5 \times 10^{-8}$M | $3 \times 10^{-6}$M | 60 | $3 \times 10^{-7}$M |

*Abbreviations are as described previously. Results are the average of at least 3 independent experiments for each compound.
**Deprenyl was the 1-isomer, while the aliphatic propargylamines tested were racemic.

b) Inhibition of MAO activities/n vivo.

Albino Swiss mice were used in this study. The animals were injected intraperitoneally with different doses of the aliphatic propargylamines in 100 µL saline. The forebrains were dissected out two hours after treatment, and MAO-A and MAO-B activities were estimated. In this study, aliphatic propargylamines with shorter carbon chain lengths (such as 2-BuMPP, 1-BuMPP, M-2-PPP and M-1-PPP) appear to be more potent than the longer chain analogs at inhibiting brain MAO-B activity (see Table 2), indicating that these smaller molecules are less easily absorbed (e.g. into lipids, membranes, etc) and more readily transported into the brain. These shorter propargylamine MAO-B inhibitors were also more effective in blocking MAO-B activity in the brain following oral administration.

TABLE 2

MAO activities in the mouse brain after intraperitoneal administration of aliphatic propargylamine MAO inhibitors.

| Inhibitors | PE $1.9 \times 10^{-5}$M $ID_{50}$ | 5-HT ($5 \times 10^{-4}$M) $ID_{50}$ | Ratio MAO-A/ MAO-B | MAO-B ID50 (mg/Kg) $IC_{50}$ ($1 \times 10^{-6}$M) |
|---|---|---|---|---|
| 2-BuMP | 1 | 20 | 20 | 1 |
| 1-BuMP | 2 | 100 | 50 | 2 |
| M-1-PP | 2 | 100 | 50 | 6.6 |
| M-2-PP | 0.5 | 25 | 50 | 2.5 |
| M-3-PP | 1.0 | 12 | 12 | 10 |
| 2-HxMP | 0.2 | 40 | 200 | 2 |
| 1-HMP | 15 | 100 | 7 | 7.5 |
| 2-HMP | 0.5 | 25 | 50 | 2.5 |
| 2-DMP | 5 | 35 | 7 | 25 |
| 2-DdMP | 4 | 60 | 15 | 100 |

TABLE 2-continued

MAO activities in the mouse brain after intraperitoneal administration of aliphatic propargylamine MAO inhibitors.

| Inhibitors | PE $1.9 \times 10^{-5}$M) $ID_{50}$ | 5-HT $(5 \times 10^{-4}$M) $ID_{50}$ | Ratio MAO-A/ MAO-B | MAO-B $ID_{50}$ (mg/Kg) $IC_{50}$ $(1 \times 10^{-6}$M) |
|---|---|---|---|---|
| Deprenyl | 0.5 | 25 | 50 | 10 |

Results are the average of 3 to 8 animals for each i.p. doses, which were 0.5, 1, 2, 5, 10, 20, 50, 100 mg/Kg. Striata were dissected from the brain two hours after i.p. administration of the drugs. MAO-A and MAO-B activities were determined immediately. The values were estimated from dose-response curves.

Table 3 indicates the MAO activities in the mouse brain following oral administration of the aliphatic propargylamines. Short chain compounds clearly exhibit superior transport properties, since although they are moderately active in inhibiting MAO-B activity in vitro, they are much more active after oral administration in comparison to Deprenyl. The longer carbon chain propargylamines, i.e. 2-DMPP and 2-DdMPP, are less potent at inhibiting MAO-B activity in vivo after acute administration (perhaps due to increased absorption). This is perhaps caused by a slower release which could be useful from a chronic treatment point of view.

TABLE 3

MAO activities in the mouse brain after oral administration of aliphatic propargylamine MAO inhibitors (10 mg/kg).

| Inhibitors | Relative activity* (%) PE $(1.9 \times 10^{-5}$M) | 5-HT $(5 \times 10^{-4}$M) | no. mice | Inhibition of MAO-B activity Dose response** $(ID_{50}$, mg/Kg) |
|---|---|---|---|---|
| Saline | 100 ± 5 | 100 ± 8 | 6 | |
| 2-BuMP | 28 ± 2 | 95 ± 11 | 6 | 5 |
| 1-BuMP | 67 ± 9 | 98 ± 5 | 3 | 15 |
| M-2-PP | 31 ± 4 | 89 ± 15 | 3 | 1 |
| M-1-PP | 72 ± 17 | 97 ± 13 | 3 | |
| 2HxMP | | | | 1 |
| 2-HMP | 39 ± 4 | 99 ± 5 | 6 | |
| 1-HMP | 118 ± 14 | 123 ± 16 | 3 | |
| 2-DMP | 104 ± 7 | 97 ± 8 | 3 | 50 |
| 2-DdMP | 64 ± 8 | 107 ± 14 | 3 | |
| Deprenyl | 40 ± 2 | 99 ± 11 | 6 | 6 |

*Results are the means ± standard errors for an oral dose of 10 mg/Kg of each compound. Striata were dissected from the brain two hours after the administration of the drugs. MAO-A and MAO-B activities were determined immediately.
**Results are the average of 5 animals for each oral dose, which were 0.5, 1, 2, 5, 10, 20, 50, 100 mg/Kg. Striata were dissected from the brain two hours after oral administration of the drugs. MAO-B activities were then determined immediately. The values were estimated from dose-response curves.

c) Evaluation of MAO-B activities for enantiomers.

The inhibitory activity of R(−) and S(+) enantiomers as well as a racemic mixture of 2-BuMP on rat liver mitochondrial MAO-B activites
toward 2phenylethylamine $(1.9 \times 10^{-5}$M) was evaluated. Results of the tests conducted are shown in FIG. 1. It can be seen from this figure that the activity of the R(−)-enantiomer is approximately 20-fold that of the S(+)-enantiomer, as far as MAO-B inhibition is concerned. This demonstrates the importance of selecting the appropriate stereoisomer in clinical pharmacology.

Neuroprotection studies

In addition to the assessment of inhibition of MAO-B activity, the following biological data demonstrates that the compounds of the present invention exhibit widespread neuroprotective properties. As exemplified herein below, the compounds of the present invention can be used to protect dopamine neurons in mice and can be used to rescue noradrenaline neurons from induced damage in mice.

a) Protection of dopamine neurons by aliphatic propargylamines against MPTP-induced neurotoxicity in the mice brain.

The analyses of MPTP-induced neurotoxicity were conducted in accordance with Heikkila et al. (Proc. Natl. Acad. Sci. U.S.A. 85 (1988), 6172–6176) hereby incorporated by reference. Mice were treated with 4×20 mg/Kg MPTP-HCl (MPTP: N-methyl-4-phenyl- 1,2,3,6-tetrahydropyridine) every 2 hours to induce depletion in the caudate nucleus. Two hours prior to MPTP challenge, aliphatic propargylamines were administered to the animals. Three days later, dopamine levels and dopamine uptake site densities (GBR bindings) were estimated. Results are shown in Table 4.

TABLE 4

Protection of dopamine neurons by aliphatic propargylamines against MPTP-induced neurotoxicity in the mice brain.

| Treatment | Dopamine (μg/gm) | Dopamine binding site (pmol/mg) |
|---|---|---|
| Saline controls | 9.0 | 312 |
| MPTP | 3.3 | 221 |
| M-2-PP (2.5 mg/Kg) + MPTP | 8.9 | 306 |
| M-2-PP (0.5 mg/Kg) + MPTP | 8.3 | 312 |
| M-1-PP (10 mg/Kg) + MPTP | 9.0 | 320 |
| M-1-PP (2.0 mg/Kg) + MPTP | 3.1 | 221 |

The mechanism of neuroprotection of the compounds of Table 4 against MPTP is as follows. MPTP (N-methyl-4-phenyl-1,2,3,6-tetrahydropyridine) is a MAO-B substrate. The compound itself has to be converted by MAO-B to MPP$^+$ (1-methyl-4-phenylpyridine) to become toxic (Chiba et al., 1984, Biochem. Biophys. Res. Comm. 120:574–578, hereby incorporated by reference). The compounds of the present invention block MAO-B activity and therefore exhibit a neuroprotective effect. It has been postulated that Parkinson's disease may be caused by MPTP-like toxins. This kind of toxin may be present in the environment or generated endogenously.

b) Protection of noradrenaline neurons by aliphatic propargylamines against DSP-4 induced neurotoxicity in the mouse brain.

The analyses of DSP-4-induced neurotoxic effects were conducted in accordance with Hallman and Jonsson (Eur. J. Pharmacol. 103 (1984), 269–278), hereby incorporated by reference. Mice were pretreated with M-2-PP (10 mg/Kg) and 2-HxMP (10 mg/Kg) or saline as control via i.p. administration and one hour later challenged with a single i.p. dose of DSP-4 (DSP-4: (N-[2-chloroethyl]-N-ethyl-2-bromobenzylamine)) (50 mg/Kg). One week after treatment noradrenaline content in the putamen of these mice was analyzed. The results which are shown in Table 5 are mean ± S.E. of five animals in each group.

TABLE 5

Protection of noradrenaline neurons by aliphatic propargylamines against DSP-4 induced neurotoxicity in the mouse brain.

| Pre-treatment | DSP-4 | Noradrenaline in putamen (%) |
|---|---|---|
| Experiment I | | |
| Saline | saline | 100 ± 0.05 |
| Saline | 50 mg/Kg | 33 ± 0.05 |
| M-2-PP (10 mg/Kg) | saline | 111 ± 0.09 |
| M-2-PP (10 mg/Kg) | 50 mg/Kg | 90 ± 0.07* |
| Experiment II | | |
| Saline | saline | 100 ± 0.07 |
| Saline | 50 mg/Kg | 56 ± 0.05 |
| 2-HxMP (10 mg/Kg) | saline | 104 ± 0.05 |
| 2-HxMP (10 mg/Kg) | 50 mg/Kg | 84 ± 0.04* |

*$p < 0.01$ t test between DSP-4 treated group and group pretreated with M-2-PPP or 2-HxMPP.

Some of the cognitive and memory impairments seen in Alzheimer's disease are possibly due to a defect of the noradrenergic system. DSP-4 is a noradrenaline neurotoxin. It is conceivable that DSP-4-like substances may be present in the environment or generated endogenously and could cause certain neurodegenerative disorders (e.g. Alzheimer's disease, accelerative aging, ischemia, etc.). The mechanism of neuroprotection by the compounds of the presentation against DSP-4 (N-(2-chloroethyl)-N-ethyl-2-bromobenzylamine) is not yet fully understood. It is, however, clear that a direct MAO-B inhibition is not involved. Unlike MPTP, DSP-4 is not a MAO-B substrate and will, therefore, not be activated by MAO-B. This indicates that the aliphatic propargylamines of the present invention are not only potent MAO-B inhibitors but can also protect against neurodegenerative disorders caused by DSP-4-like compounds.

Another explanation regarding the neuroprotective property of the compounds of the present invention could be based on an oxidative stress theory that has been recently proposed (Youdim et al., 1990, J. Neural Transm. 32:239–248). During MAO-catalyzed deamination hydrogen peroxide is also formed as a side product. Such hydrogen proxide, in the presence of iron ions, can lead to formation of the very toxic hydroxyl free radical. It appears that excessive MAO-catalyzed deamination might occur in the brain in neurodegenerative conditions (e.g. Parkinson's and Alzheimer's diseases), therefore, excess free radicals can be formed and thus cause neuronal damage. Application of the compounds of the present invention to inhibit MAO-B activity can reduce such oxidative stress and therefore can be useful in the protection against such neuronal degeneration.

c) Rescue of dying neurons with aliphatic proparglamines.

In presently ongoing studies, mice were treated with MPTP for 5 days, then with no drug for 3 days and then with either M-2-PP or 2-HxMP three times weekly for a further three weeks. The extent of neuronal degeneration, or death, was assessed by tyrosine hydroxylase staining, Nissl staining or estimation of dopamine and dopamine metabolites in the striata and/or substantia nigra. The drugs were found to be effective in reducing the extent of (i.e. rescuing) damage caused by the MPTP toxin. The protocol for this study was similar to that described by Tatton and Greenwood (1991, Rescue of dying neurones in a new action for deprenyl in MPTP Parkinsonism, J. Neurosci. Res. 30, p. 666–672, hereby incorporated by reference).

Toxicity and hypertensive effect.

The aliphatic propargylamines described above are not only highly potent and specific with respect to inhibition of MAO-B activity (Tables 1 to 3), they also do not possess an amphetamine-like residue within their structure. Thus, they represent a substantial improvement over already available MAO-B inhibitors and they cannot produce amphetaminergic side-effects, as a result of metabolic breakdown. Furthermore, because these compounds are highly selective MAO-B inhibitors, like Deprenyl, they will not cause the hypertensive reaction usually observed with MAO-A inhibitors.

The acute toxicity of these compounds is quite low. In toxicity studies performed with some of the compounds disclosed in the examples, namely 2-BuMPP, 1-BuMPP, M-2-PPP and M-1-PPP, oral administration to mice at doses up to 1000 mg/kg resulted in no fatality. This is significantly less toxic than Deprenyl, for which the $LD_{50}$ has been reported to be 445 mg/Kg. The aliphatic side-chains of these aliphatic propargyl compounds are similar to those that exist in endogenous lipids and fatty acids and such aliphatic chains are readily oxidized in vivo. The major metabolic products of Deprenyl are methamphetamine or amphetamine which probably arise by hydroxylation and cleavage between the propargyl and the amphetamine moieties. Aliphatic propargylamines are likely to be hydrolyzed in a similar manner. 1-BuMPP, for instance, would be hydrolyzed to n-butylamine, which is then deaminated to form n-butylaldehyde and subsequently oxidized to the totally non-toxic n-butyric acid.

Formulations and dosages.

The compounds of the present invention can be used in human and veterinary therapy for the treatment of various diseases of the central nervous system and consequently a formulation could include all pharmaceutical compositions containing the aliphatic propargylamines referred to above as active principals, in association with any excipients which are suitable for their administration. In oral administration, the compounds may be administered as tablets, coated tablets, gelatine capsules, capsules, cachets, and solutions or suspensions to be taken orally. The compounds can also be administered parenterally or through any other suitable administrative route such as intravenous, subcutaneous, depot injections, intramuscular, intrathecal, intraventricular, intra-articular, rectal (suppository, enema), sublingual, buccal, intra-ocular, intra-vitreo, transdermal (this is the skin patch), nasal drops (nebuliser, infufflation), liposomal delivery systems. The daily dosages could likely range from 1 to 100 mg.

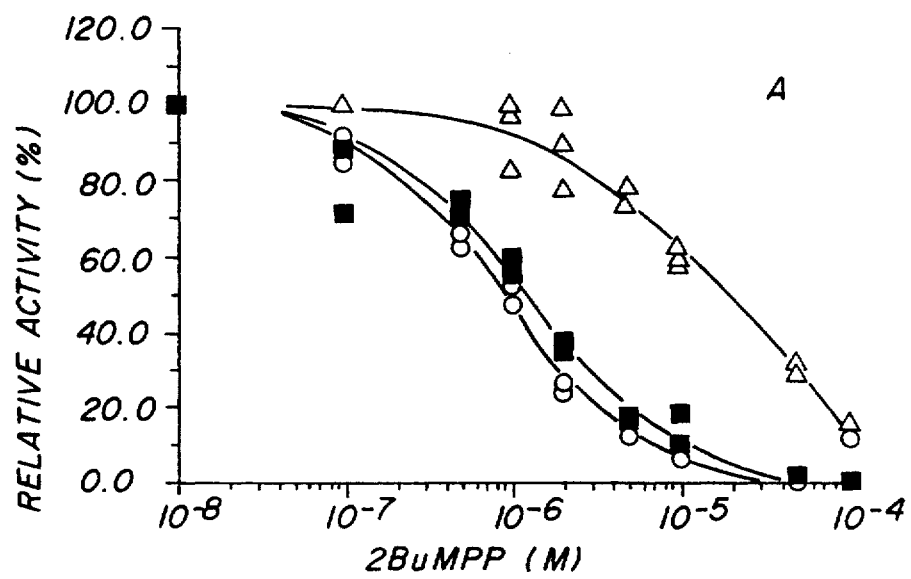

We claim:

1. A compound having the following formula

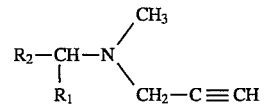

wherein $R_1$ is hydrogen or a straight chain or branched lower alkyl; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, lower acyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and/or N, or $R_2$ is a straight chain or branched alkyl group having 1, 2, 12, 13 or 14 carbon atoms which is unsubstituted or is substituted by halogen and pharmaceutically acceptable salts thereof, with the provisos that:

when $R_1$ is $CH_3$, $R_2$ is not an unsubstituted alkyl having from 4 to 7 carbon atoms, and when $R_2$ is substituted with carboxyl or loweracyloxy, the carboxyl or loweracyloxy substituent is not on the last atom of the longest chain of the $R_2$ group.

2. A compound according to claim 1 wherein $R_1$ is a lower alkyl having between 1 and 4 carbon atoms and $R_2$ is a straight chain or branched alkyl, alkenyl, alkynyl or alkoxy, unsubstituted or substituted with at least one halogen selected from the group consisting of fluorine, chlorine, bromine and iodine.

3. A compound according to claim 1, wherein $R_2$ has the following formula:

wherein x is an integer ranging from 1 to 2 or 7 to 13;

R' represents H or halogen; and

R" represents methyl, hydrogen or halogen.

4. A compound according to claim 1, selected from the group consisting of:

N-(1-butyl)-N-methylpropargylamine-HCl (1-BuMP)
N-(2-butyl)-N-methylpropargylamine-HCl (2-BuMP)
N-(2-pentyl)-N-methylpropargylamine-HCl (M-2-PP)
N-(1-pentyl)-N-methylpropargylamine-oxalate (M-1-PP)
N-(2-decyl)-N-methylpropargylamine-HCl (2-DMP)
N-(2-dodecyl)-N-methylpropargylamine-HCl (2-DdMP) and
R(-)-N-(2-butyl)-N-methylpropargylamine-oxalate (R-(-) 2-BuMP).

5. A pharmaceutical composition for the in vivo inhibition of MAO-B activity in mammals, said composition comprising an effective amount of a compound having the following formula:

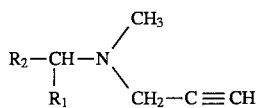

wherein $R_1$ is hydrogen or a straight chain or branched lower alkyl; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or $R_2$ is a straight chain or branched alkyl group having 1, 2, 12, 13 or 14 carbon atoms which is unsubstituted or is substituted by halogen and pharmaceutically acceptable salts thereof, in admixture with a pharmaceutically acceptable carrier, excipient or adjuvant, with the provisos that:

when $R_1$ is $CH_3$, $R_2$ cannot be an unsubstituted alkyl having from 4 to 7 carbon atoms, and when $R_2$ is substituted with carboxyl or loweracyloxy, the carboxyl or loweracyloxy substituent is not on the last atom of the longest chain of the $R_2$ group, in admixture with a pharmaceutically acceptable carrier, excipient or adjuvant.

6. A pharmaceutical composition according to claim 5, wherein in said compound of formula I, $R_1$ is a lower alkyl having between 1 and 4 carbon atoms and $R_2$ is a straight chain or branched alkyl, alkenyl, alkynyl or alkoxy, unsubstituted or substituted with at least one halogen selected from the group consisting of fluorine, chlorine, bromine and iodine.

7. A pharmaceutical composition according to claim 5, wherein $R_2$ has the following formula:

wherein x is an integer ranging from 1 to 2 or 7 to 13;

R' represents H or halogen; and

R" represents methyl, hydrogen or halogen.

8. A pharmaceutical composition according to claim 5, wherein said compound of formula I is selected from the group consisting of:

N-(1-butyl)-N-methylpropargylamine-HCl (1-BuMP)
N-(2-butyl)-N-methylpropargylamine-HCl (2-BuMP)
N-(2-pentyl)-N-methylpropargylamine-HCl (M-2-PP)
N-(1-pentyl)-N-methylpropargylamine-oxalate (M-1-PP)
N-(2-decyl)-N-methylpropargylamine-HCl (2-DMP)
N-(2-dodecyl)-N-methylpropargylamine-HCl (2-DdMP) and
R(-)-N-(2-butyl)-N-methylpropargylamine-oxalate (R-(-) 2-BuMP).

9. A pharmaceutical composition for the treatment and prevention of neurodegenerative disorders in mammals, said composition comprising an effective amount of a compound having the following formula:

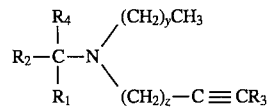

wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or $R_2$ is a straight chain or branched alkyl group having 1, 2, 12, 13 or 14 carbon atoms which is unsubstituted or is substituted by halogen and pharmaceutically acceptable salts thereof, in admixture with a pharmaceutically acceptable carrier, excipient or adjuvant, with the provisos that:

when $R_1$ is $CH_3$, $R_2$ cannot be an unsubstituted alkyl having from 4 to 7 carbon atoms, and when $R_2$ is substituted with carboxyl or loweracyloxy, the carboxyl or loweracyloxy substituent is not on the last atom of the longest of the $R_2$ group.

10. A pharmaceutical composition according to claim 9, wherein in said compound of formula I, $R_1$ is a lower alkyl having between 1 and 4 carbon atoms, $R_2$ is a straight chain or branched alkyl, alkenyl, alkynyl or alkoxy, unsubstituted or substituted with at least one halogen selected from the group consisting of fluorine, chlorine, bromine and iodine, $R_3$ and $R_4$ are hydrogen and y and z are 0.

11. A pharmaceutical composition according to claim 9, wherein $R_2$ has the following general formula:

$$R''(CR'_2)_x-$$

wherein x is an integer ranging from 1 to 2 or 7 to 13;

R' represents H or halogen; and

R" represents methyl, hydrogen or halogen.

12. A pharmaceutical composition according to claim 9, wherein said compound of formula III is selected from the group consisting of:
N-(1-butyl)-N-methylpropargylamine-HCl (1-BuMP)
N-(2-butyl)-N-methylpropargylamine-HCl (2-BuMP)
N-(2-pentyl)-N-methylpropargylamine-HCl (M-2-PP)
N-(1-pentyl)-N-methylpropargylamine-oxalate (M-1-PP)
N-(2-decyl)-N-methylpropargylamine-HCl (2-DMP)
N-(2-dodecyl)-N-methylpropargylamine-HCl (2-DdMP)
and
R(−)-N-(2-butyl)-N-methylpropargylamine-oxalate (R-(−)-2-BuMP).

13. A method for the in vivo inhibition of MAO-B to alleviate neuropsychiatric disorders in mammalian subjects which comprises administering to a mammalian subject in need thereof a compound having the following formula I:

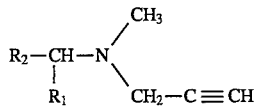

wherein $R_1$ is hydrogen or a straight chain or branched lower alkyl; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or $R_2$ is a straight chain or branched alkyl group having 1, 2, 12, 13 or 14 carbon atoms which is unsubstituted or is substituted by halogen and pharmaceutically acceptable salts thereof, with the provisos that:

when $R_2$ is substituted with carboxyl or loweracyloxy, the carboxyl or loweracyloxy substituent is not on the last carbon atom of the $R_2$ chain, in admixture with a pharmaceutically acceptable carrier, excipient or adjuvant, for the in vivo inhibition of MAO-B to alleviate neuropsychiatric disorders in mammalian subjects.

14. A method according to claim 13, wherein in said compound of formula I, $R_1$ is a lower alkyl having between 1 and 4 carbon atoms and $R_2$ is a straight chain or branched alkyl, alkenyl, alkynyl or alkoxy, unsubstituted or substituted with at least one halogen selected from the group consisting of fluorine, chlorine, bromine and iodine.

15. Use according to claim 13, wherein $R_2$ in said compound of formula has the following formula:

$$R''(CR'_2)_x-$$

wherein x is an integer ranging from 1 to 13;

R' represents H or halogen; and

R" represents methyl, hydrogen or halogen.

16. A method according to claim 13, wherein said compound of formula I is selected from the group consisting of:
N-(1-butyl)-N-methylpropargylamine-HCl (1-BuMP)
N-(2-butyl)-N-methylpropargylamine-HCl (2-BuMP)
N-(2-pentyl)-N-methylpropargylamine-HCl (M-2-PP)
N-(1-pentyl)-N-methylpropargylamine-oxalate (M-1-PP)
N-(2-hexyl)-N-methylpropargylamine-HCl (2-HxMP)
N-(2-heptyl)-N-methylpropargylamine-HCl (2-HMP)
N-(2-decyl)-N-methylpropargylamine-HCl (2-DMP)
N-(2-dodecyl)-N-methylpropargylamine-HCl (2-DdMP)
and
R(−)-N-(2-butyl)-N-methylpropargylamine-oxalate (R-(−)-2-BuMP).

17. A method for the in vivo inhibition of MAO-B to alleviate neuropsychiatric disorders in mammalian subjects which comprises administering to a mammalian subject in need thereof a compound having the following formula III:

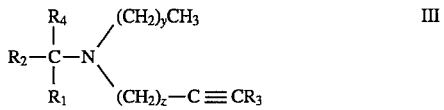

wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or $R_2$ is a straight chain or branched alkyl group having 1, 2, 12, 13 or 14 carbon atoms which is unsubstituted or is substituted by halogen and pharmaceutically acceptable salts thereof, in admixture with a pharmaceutically acceptable carrier, excipient or adjuvant in preventing the premature degeneration of neuron cells in mammalian subject.

18. A method according to claim 17, wherein in said compound of formula III, $R_1$ is a lower alkyl having between 1 and 4 carbon atoms, $R_2$ is a straight chain or branched alkyl, alkenyl, alkynyl or alkoxy, unsubstituted or substituted with at least one halogen selected from the group consisting of fluorine, chlorine, bromine and iodine, $R_3$ and $R_4$ are hydrogen and y is 0 and z is 1.

19. A method according to claim 18, wherein $R_2$ has the following formula:

$$R''(CR'_2)_x-$$

wherein x is an integer ranging from 1 to 13;

R' represents H or halogen; and

R" represents methyl, hydrogen or halogen.

20. Use according to claim 17, wherein said compound of formula III is selected from the group consisting of:

N-(2-pentyl)-N-methylpropargylamine-HCl (M-2-PP)

N-(1-pentyl)-N-methylpropargylamine-oxalate (M-1-PP) and

N-(2-hexyl)-N-methylpropargylamine-HCl (2-HxMP).

21. A method for the in vivo inhibition of MAO-B to alleviate neuropsychiatric disorders in mammalian subjects which comprises administering to a mammalian subject in need thereof a compound having the following formula III:

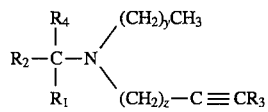   III wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, and pharmaceutically acceptable salts thereof, in admixture with a pharmaceutically acceptable carrier, excipient or adjuvant in protecting mammalian neuron cells from the action of neurotoxic agents causing neurodegenerative disorders to mammals.

22. A method according to claim 21, wherein in compound of formula III, $R_1$ is a lower alkyl having between 1 and 4 carbon atoms, $R_2$ is a straight chain or branched alkyl, alkenyl, alkynyl or alkoxy, unsubstituted or substituted with at least one halogen selected from fluorine, chlorine, bromine and iodine, $R_3$ and $R_4$ are hydrogen and y is 0 and z is 1.

23. A method according to claim 22, wherein $R_2$ has the following formula:

wherein x is an integer ranging from 1 to 13;

R' represent H or halogen; and

R" represents methyl, hydrogen or halogen.

24. A method for the in vivo inhibition of MAO-B to alleviate neuropsychiatric disorders in mammalian subjects which comprises administering to a mammalian subject in need thereof according to claim 21, wherein said compound of formula III is selected from the group consisting of:

N-(2-pentyl)-N-methylpropargylamine-HCl (M-2-PP)

N-(1-pentyl)-N-methylpropargylamine-oxalate (M-1-PP) and

N-(2-hexyl)-N-methylpropargylamine-HCl (M-HxMP).

25. A method for the in vivo inhibition of MAO-B to alleviate neuropsychiatric disorders in mammalian subjects which comprises administering to a mammalian subject in need thereof a compound having the following formula III:

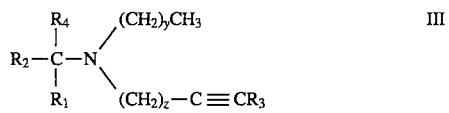   III wherein $R_1$, $R_3$ and $R_4$ are the same or different and represent hydrogen or a straight chain or branched lower alkyl;

y is an integer ranging from 0 to 5;

z is an integer ranging from 0 to 5; and $R_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or $R_2$ is a straight chain or branched alkyl group having 1, 2, 12, 13 or 14 carbon atoms which is unsubstituted or is substituted by halogen and pharmaceutically acceptable salts thereof, in admixture with a pharmaceutically acceptable carrier, excipient or adjuvant, in the treatment of neurodegenerative disorders in mammals.

26. A method according to claim 25, wherein in compound of formula III, $R_1$ is a lower alkyl having between 1 and 4 carbon atoms, $R_2$ is a straight chain or branched alkyl, alkynyl or alkoxy, unsubstituted or substituted with at least one halogen selected from the group consisting of fluorine, chlorine, bromine and iodine, $R_3$ and $R_4$ are hydrogen and y is 0 and z is 1.

27. A method according to claim 26, wherein $R_2$ has the following formula:

wherein x is an integer ranging from 1 to 13;

R' represents H or halogen; and

R" represents methyl, hydrogen or halogen.

28. A method according to claim 25, wherein said compound of formula III is selected from the group consisting of:

N-(2-pentyl)-N-methylpropargylamine-HCl (M-2-PP)

N-(1-pentyl)-N-methylpropargylamine-oxalate (M-1-PP) and

N-(2-hexyl)-N-methylpropargylamine-HCl (2-HxMP).

29. A commercial package for the in vivo inhibition of MAO-B to alleviate neuropsychiatric disorders in mammalian subjects, said package comprising a pharmaceutical agent therapeutically effective for the in vivo inhibition of MAO-B to alleviate neuropsychiatric disorders in mammals together with instructions to use said pharmaceutical agent in the in vivo inhibition of MAO-B to alleviate neuropsychiatric disorders in mammals, said pharmaceutical agent comprised in said commercial package having the following formula:

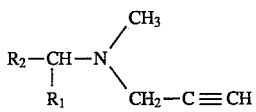 I wherein

R$_1$ is hydrogen or a straight chain or branched lower alkyl; and

R$_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or R$_2$ is a straight chain or branched alkyl group having 1, 2, 12, 13 or 14 carbon atoms which is unsubstituted or is substituted by halogen and pharmaceutically acceptable salts thereof, with the provisos that:

when R$_2$ is substituted with carboxyl or loweracyloxy, the carboxyl or loweracyloxy substituent is not on the last carbon atom of the R$_2$ chain.

30. A commercial package for the treatment or prevention of neurodegenerative disorders in mammals, said package comprising a pharmaceutical agent therapeutically effective for the treatment or prevention of neurodegenerative disorders in mammals together with instructions to use said pharmaceutical agent in the treatment or prevention of neurodegenerative disorders in mammals, said pharmaceutical agent comprising in said commercial package having the following formula:

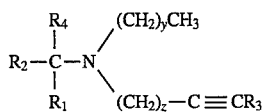 III wherein

R$_1$, R$_3$ and R$_4$ are the same or different and represent hydrogen or a straight chain or branched lower alkyl;

y is an integer ranging from 0 to 5;

z is an integer ranging from 0 to 5; and

R$_2$ is a straight chain or branched alkyl, alkenyl, alkynyl, alkoxy, alkylthio or alkyl sulphinyl group having from 3 to 11 carbon atoms, said group being unsubstituted or substituted with at least one of the substituents selected from the group consisting of hydroxy, aldehyde, oxo, loweracyloxy, halogen, thio, sulfoxide, sulfone, phenyl, halogen-substituted phenyl, hydroxy-substituted phenyl, cycloalkyl having from 3 to 6 carbon atoms and heterocyclic substituents having between 3 and 6 atoms, of which from 1 to 3 are heteroatoms selected from the group consisting of O, S and N, or R$_2$ is a straight chain or branched alkyl group having 1, 2, 12, 13 or 14 carbon atoms which is unsubstituted or is substituted by halogen.

\* \* \* \* \*

UNITED STATES PATENT AND TRADEMARK OFFICE
CERTIFICATE OF CORRECTION

PATENT NO. : 5,508,311  
DATED : April 16, 1996  
INVENTOR(S) : YU et al

PAGE 1 of 3

It is certified that error appears in the above-indentified patent and that said Letters Patent is hereby corrected as shown below:

The Drawing sheet consisting of Figure 1, should be inserted as per attached sheet.

Column 31, line 59, before "N" delete "and" and substitute therefor --and/or--.

Column 32, line 57, before "N" delete "and" and substitute therefor --and/or--.

Column 33, line 50, before "N" delete "and" and substitute therefor --and/or--.

Column 33, lines 59-61, delete ", for the in vivo... mammalian subjects".

Column 34, line 1, change "Use" to "A method".

line 2, after "formula" insert --I--.

Column 34, line 47, before "N" delete "and" and substitute therefor --and/or--.

Column 34, lines 52-54, delete "in preventing ... in mammalian subject".

Column 35, line 4, change "Use" to --A method--.

Column 35, lines 11-12, delete "for the in vivo ... mammalian subjects" and substitute therefor --of protecting mammalian neuron cells from the action of neurotoxic agents causing neurodegenerative disorders to mammals--.

UNITED STATES PATENT AND TRADEMARK OFFICE
CERTIFICATE OF CORRECTION

PATENT NO. : 5,508,311
DATED : April 16, 1996
INVENTOR(S) : YU et al

It is certified that error appears in the above-indentified patent and that said Letters Patent is hereby corrected as shown below:

Column 35, line 36, after "N" insert --or $R_2$ is a straight chain or branched alkyl group having 1, 2, 12, 13 or 14 carbon atoms which is unsubstituted or is substituted by halogen--.

Column 35, line 36, before "N" delete "and" and substitute therefor --and/or--.

Column 35, lines 39-42, delete "in protecting mammalian ... disorders to mammals".

Column 35, line 47, after "halogen selected from" insert --the group consisting of--.

Column 35, line 67, delete "(M-HxMP)" to --(2-HxMP)-.

Column 36, line 27, before "N" delete "and" and substitute therefor --and/or--.

Column 36, lines 32-33, delete ", in the treatment of neurodegenerative disorders in mammals".

Column 37, line 12, after "substituents" insert --selected from--.

Column 37, line 19, before "N" delete "and" and substitute therefor --and/or--.

Column 38, line 3, delete "comprising in" and substitute therefor comprised in--.

Column 38, line 26, before "N" delete "and" and substitute therefor --and/or--.

Signed and Sealed this

Eighteenth Day of November 1997

Attest:

BRUCE LEHMAN

Attesting Officer

Commissioner of Patents and Trademarks